United States Patent [19]

Shibanuma et al.

[11] Patent Number: 4,608,373
[45] Date of Patent: Aug. 26, 1986

[54] CEPHEM COMPOUNDS

[75] Inventors: Tadao Shibanuma; Kohji Nakano; Noriaki Nagano; Yukiyasu Murakami, all of Saitama; Ryuichiro Hara, Tokyo, all of Japan

[73] Assignee: Yamanouchi Pharmaceutical Co., Ltd., Tokyo, Japan

[21] Appl. No.: 560,412

[22] Filed: Dec. 12, 1983

[30] Foreign Application Priority Data

Dec. 13, 1982 [JP] Japan ................................ 57-218208
Mar. 28, 1983 [JP] Japan ................................ 58-52067
Mar. 28, 1983 [JP] Japan ................................ 58-52068
Oct. 7, 1983 [JP] Japan ................................ 58-188619
Oct. 11, 1983 [JP] Japan ................................ 58-189555

[51] Int. Cl.$^4$ ................... C07D 501/34; A61K 31/545
[52] U.S. Cl. ..................................... 514/202; 514/206; 514/205; 540/224; 540/227; 540/228
[58] Field of Search .................... 544/25, 21, 26, 27, 544/22, 28, 24; 424/246; 514/203, 205, 206, 207

[56] References Cited

U.S. PATENT DOCUMENTS 4,399,131 8/1983 Dürckheimer et al. ............. 424/246
4,416,879 11/1983 Takaya et al. ..................... 544/27

FOREIGN PATENT DOCUMENTS 0112164 12/1982 European Pat. Off. .

Primary Examiner—Nicholas S. Rizzo
Attorney, Agent, or Firm—Burgess, Ryan & Wayne

[57] ABSTRACT

Novel cephem compounds are provided having the formula:

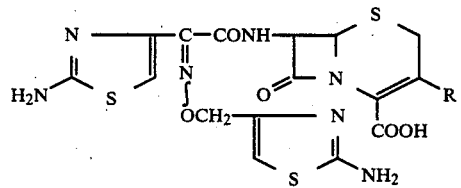

wherein R represents lower alkyl, which may be substituted with lower acyloxy, lower alkylthio or certain 5 or 6-membered heterocyclic ring-containing groups. The cephem compounds and salts thereof exhibit antibacterial activity to many pathogens. A process for producing the cephem compounds is also provided.

7 Claims, No Drawings

CEPHEM COMPOUNDS

DETAILED DESCRIPTION OF THE INVENTION

This invention relates to novel cephem compounds and the salts thereof. More particuarly, the invention relates to novel cephem compounds having antibacterial activity and the salts thereof as well as to a process of producing these compounds and further to therapeutic compositions containing these compounds.

That is, one object of this invention is to provide novel cephem compounds having activity to many pathogens and the salts thereof.

Other object of this invention is to provide a process of producing novel cephem compounds and the salts thereof.

Another object of this invention is to provide therapeutic compositions containing the foregoing novel cephem compounds or the salts thereof as effective components.

The cephem compounds of this invention are novel compounds shown by the general formula I

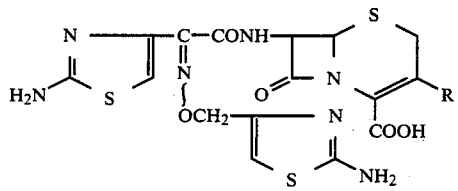

wherein R represents a lower alkyl group, which may be substituted by a lower acyloxy group, a lower alkylthio group,

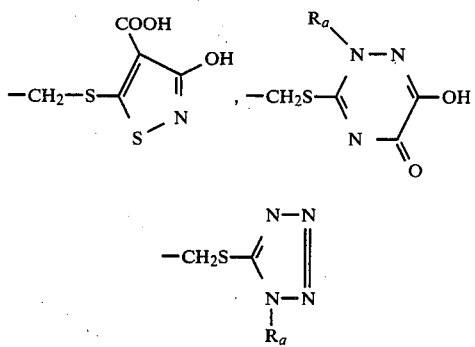

(wherein $R_a$ represents a hydrogen atom or a lower alkyl group),

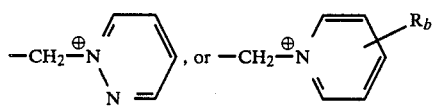

[wherein $R_b$ represents a hydrogen atom, $(CH_2)_mCOOH$, $(CH_2)_mOH$, $(CH_2)_mNH_2$, $(CH_2)_mSO_3H$, or CONH—R' (R' represents a hydrogen atom, a hydroxy group or $(CH_2)_nCOOH$, m is 0 or an integer of 1 to 3, and n is an integer of 1 to 3)] and the salts of the cephem compounds.

Many cephem compounds having an α-(substituted-)oxyimino-α-(2-amino-4-thiazolyl)acetamido moiety at the substituent of the 7-position are known as described in, for example, U.S. Pat. No. 4,336,253, DE 2,921,316, EP 55,466, EP 57,422, EP 58,250, EP 74,645, EP 75,805, etc. However, cephem compounds having an α-(2-amino-4-thiazolyl)methoxyimino)-α-(2-amino)-4-thiazolyl)acetamido group as a substituent at the 7-position are not known and are first provided by the present invention.

The term "lower" in the foregoing definition of general formula I means a straight or branched carbon chain having 1 to 5 carbon atoms. Therefore, examples of the "lower alkyl group" are a methyl group, an ethyl group, a propyl group, an isopropyl group, a butyl group, an isobutyl group, a tert-butyl group, an amyl group, an isopentyl group, a 1-methyl-butyl group, a neopentyl group, etc., and examples of the "lower acyloxy group" are an actoxy group, a propionyloxy group, a butyryloxy group, an isobutyryloxy group, etc. Thus acyls are acetyl, propionyl, n- or iso-butyryl, etc.

The salts of the cephem compounds shown by general formula I are the pharmaceutically acceptable nontoxic salts of the cephem compounds and examples of these salts are salts of inorganic bases, e.g., an alkali metal such as sodium, potassium, etc., and an alkaline earth metal such as calcium, manganese, etc.; ammonium salts; salts of organic bases such as trimethylamine, triethylamine, cyclohexylamine, dicyclohexylamine, diethanolamine, or basic amino acids such as arginine, lysine, etc.; salts of inorganic acids such as mineral acid such as hydrochloric acid, sulfuric acid, phosphoric acids, etc.; and salts of organic acids such as acetic acid, trifluoroacetic acid, lactic acid, tartaric acid, fumaric acid, maleic acid, methanesulfonic acid, ethanesulfonic acid, etc.

The compounds of this invention shown by formula I have an iminoether-type oxime and 2-substituted thiazol group and these compounds include geometrical isomers and tautomers. The compounds of this invention include all these syn-form and anti-form geometrical isomers and tautomers.

When a cationic substituent is included in the substituent at the 3-position of the compounds of general formula I, the carboxy group at the 4-position is in the form of a carboxylate anion.

The compounds of this invention shown by formula I show antibacterial activities to various pathogens and, in particular have excellent effects to several important gram positive pathogens. Accordingly, the compounds of this invention are useful as medicaments, in particular, antibacterial agents.

Antibacterial activities (minimum effective inhibitory concentrations) of the compounds of formula I are shown in the following table in comparison with those of cefatazidime having the structure

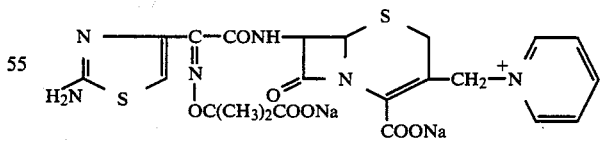

and cefmenoxime having the structure

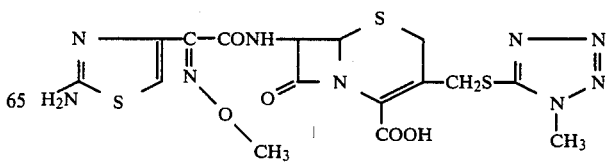

TABLE

MIC (γ/ml)

| Strain | 1(b) | 2(b) | 3(b) | 5 | 6 | 7 | 8 | 9 | 12 | 13 | 14 | 15 | 16 | 17 | 18 | 19 | 20 | 21 | 22 | 23 | CD | CX |
|---|---|---|---|---|---|---|---|---|---|---|---|---|---|---|---|---|---|---|---|---|---|---|
| Staph. aureus ATCC 6538P | 3.13 | 1.56 | 0.78 | 3.13 | 0.78 | 1.56 | 1.56 | 1.56 | 3.13 | 3.13 | 3.13 | 1.56 | 3.13 | 6.25 | 0.78 | 0.78 | 6.25 | 0.39 | 1.56 | 3.13 | 6.25 | 3.13 |
| Staph. aureus Smith | 6.25 | 1.56 | 0.78 | 3.13 | 0.78 | 1.56 | 0.78 | 1.56 | 3.13 | 3.13 | 3.13 | 1.56 | 6.25 | 6.25 | 0.78 | 0.78 | 6.25 | 0.39 | 1.56 | 6.25 | 6.25 | 6.25 |
| Staph. aureus Terashima | 12.5 | 3.13 | 1.56 | 12.5 | 1.56 | 1.56 | 1.56 | 1.56 | 6.25 | 6.25 | 6.25 | 1.56 | 6.25 | 12.5 | 1.56 | 0.78 | 12.5 | 0.39 | 3.13 | 3.13 | 12.5 | 12.5 |
| E. coli Ebara | 1.56 | ≦0.2 | 3.13 | ≦0.2 | ≦0.2 | 0.78 | 0.78 | ≦0.2 | 1.56 | 3.13 | 3.13 | ≦0.2 | 1.56 | 12.5 | 0.78 | 0.39 | 6.25 | ≦0.2 | 1.56 | 0.39 | ≦0.2 | 0.2 |
| Kleb. pneumoniae ATCC 10031 | ≦0.2 | ≦0.2 | ≦0.2 | ≦0.2 | ≦0.2 | ≦0.2 | ≦0.2 | ≦0.2 | ≦0.2 | ≦0.2 | ≦0.2 | ≦0.2 | ≦0.2 | 0.39 | ≦0.2 | ≦0.2 | 0.39 | ≦0.2 | ≦0.2 | ≦0.2 | ≦0.2 | ≦0.2 |
| Proteus morgani IID 602 | 3.13 | 0.39 | 1.56 | 0.39 | 0.39 | 1.56 | 0.78 | 0.39 | 0.78 | 1.56 | 0.78 | 1.56 | 0.78 | 1.56 | 0.78 | 0.78 | 1.56 | 0.39 | 1.56 | 0.78 | ≦0.2 | ≦0.2 |
| Serr. marcescens IID 620 | 1.56 | 0.78 | 1.56 | 0.78 | 0.39 | 0.39 | 0.78 | 0.78 | ≦0.2 | ≦0.2 | ≦0.2 | ≦0.2 | 0.39 | 0.39 | 0.39 | ≦0.2 | ≦0.2 | ≦0.2 | 0.78 | 0.39 | ≦0.2 | 0.2 |
| Ent. aerogenes ATCC 13048 (MS-1) | 6.25 | 1.56 | 6.25 | 1.56 | 1.56 | 3.13 | 1.56 | 1.56 | 1.56 | 3.13 | 1.56 | 1.56 | 3.13 | 3.13 | 1.56 | 1.56 | 3.13 | 0.78 | 3.13 | 1.56 | 0.39 | / |
| Ent. cloacae V-8 | 6.25 | 3.13 | 3.13 | 1.56 | 1.56 | 6.25 | 6.25 | 3.13 | 3.13 | 3.13 | 3.13 | 3.13 | 6.25 | 6.25 | 3.13 | 3.13 | 12.5 | 1.56 | 6.25 | 3.13 | 1.56 | 3.13 |
| Ps. aeruginosa NCTC 10490 | 6.25 | 0.39 | 1.56 | 1.56 | ≦0.2 | 0.78 | ≦0.2 | 0.39 | 1.56 | 1.56 | 0.39 | ≦0.2 | 1.56 | 1.56 | 0.39 | 0.78 | 1.56 | 0.39 | 1.56 | 0.39 | 0.78 | 1.56 |
| Ps. aeruginosa IID 5142 | / | 25 | / | 12.5 | 12.5 | 12.5 | 3.13 | 6.25 | 25 | 25 | 12.5 | 6.25 | 25 | 25 | 6.25 | 6.25 | 25 | 6.25 | 12.5 | 6.25 | 1.56 | 100 |

CD—Ceftazidime
CX—Cefmenoxime

Antibacterial agents containing the compounds shown by general formula I or the salts thereof as the main components are prepared by optional conventional methods using conventional carriers or excipients for preparation. They may be orally administered as tablets, pills, capsules, granules, etc., or may be parenterally administered by intravenous injection, intramuscular injection, etc., or as suppositories. The doses of the antibacterial agents are properly determined according to each case considering the symptoms, age, sex distinction, etc., of patient but usually 250 to 3,000 mg per day for an adult and are administered one to 4 times a day.

The compounds of this invention can be produced by various processes and typical productions processes are explained hereinafter.

Process 1:

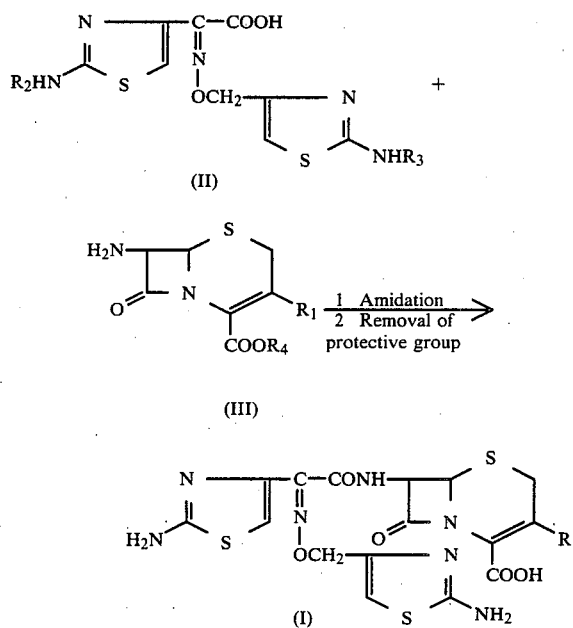

wherein $R_1$ represents R (as defined in the foregoing general formula I) and R the carboxy of which is protected; and $R_2$, $R_3$, and $R_4$ each represents hydrogen atom or a protective group.

The compounds shown by general formula I can be produced by reacting a substituted oxyiminothiazolylacetic acid derivative shown by general formula II or reactive derivative thereof and a 7-amino-3-cephem derivative shown by general formula III and then, if desired, releasing a protective group.

In this case, the protective group for an amino group means a protective group usually used in the field of said peptide chemistry and practical examples are acyl groups such as a formyl group, an acetyl group, a propionyl group, a tert-butoxycarbonyl group, a methoxyacetyl group, methoxypropionyl group, a benzyloxycarbonyl group, a p-nitrobenzyloxycarbonyl group, etc., and aralkyl groups such as a benzyl group, a benzhydryl group (diphenylmethyl group), a trityl group, etc.

Also, practical examples of the protective group for the carboxy group are the protective group, which can be easily released under a mild condition, such as a trimethylsilyl group, a benzhydryl group, a β-methylsulfonylethyl group, a phenacyl group, a p-methoxybenzyl group, a tert-butyl group, a p-nitrobenzyl group, etc.

The reaction is usually performed in a solvent under cooling at a temperature below room temperature including room temperature.

Any solvents which do not take part in the reaction can be used in this invention. Examples of the solvents usually used in this invention are organic solvents such as dioxane, tetrahydrofuran, ether, acetone, ethyl methyl ketone, chloroform, dichloromethane, dichloroethane, methanol, ethanol, acetonitrile, ethyl acetate, ethyl formate, dimethylformamide, dimethyl sulfoxide, etc. These solvents may be used solely or as a proper mixture of them.

The compounds shown by formula II are used in the state of a free carboxylic acid or may be used in the reaction as a reactive derivative of carboxylic acid. Suitable examples of the compounds are mixed acid anhydrides, acid anhydrides, acid halides, active esters, active amide, acid azides, etc. In the case of using the compound of formula II as the state of a free carboxylic acid, it is preferred to use a condensing agent such as N,N'-dichlorohexylcarbodiimide, N,N'-diethylcarbodiimide, etc.

Also, according to the kind of the reactive derivative of the carboxylic acid used, it is as the case may be preferred for smoothly proceeding the reaction to perform the reaction in the presence of a base. Examples of such a base are inorganic bases such as sodium hydrogen-carbonate, potassium hydrogencarbonate, sodium carbonate, potassium carbonate, etc.; and organic bases such as trimethylamine, triethylamine, dimethylaniline, pyridine, etc.

The removal of the protective group for the amino group from the reaction product thus obtained can be easily performed, in the case of using the foregoing aralkyl groups such as a trityl group, etc., or various acyl groups as the protective group, by the hydrolysis with an acid. As the acid used in this case, formic acid, trifluoroacetic acid, hydrochloric acid, etc., are preferred. Also, the removal of the protective group for the carboxy group can be easily performed using an acid in the case of a benzhydryl group, p-methoxybenzyl group, etc., or by the contact with water in the case of a trimethylsilyl group.

In addition, the removal of the protective group for the carboxy group can be performed simultaneously with the removal of the protective group for the amino group.

The salts of the compounds of this invention shown by general formula I can be produced by performing the foregoing production process using previously a salt of the raw material compound or alternatively by applying a salt-forming reaction, which is usually practiced in the field of the art, to the free compound produced by the foregoing production process.

For example, the alkali metal salt can be produced by adding a n-butanol solution of an alkali 2-ethylhexanoate to the reaction product and then adding thereto an organic solvent having different solubility, such as ether, ethyl acetate, etc.; the salt of an organic base or a basic amino acid can be obtained by adding an equivalent amount or a lightly excessive amount of an organic base or a basic amino acid such as dicyclohexylamine, triethylamine, cyclohexylamine, diethanolamine, alginine, lysine, etc., to the reaction product and the ammonium salt can be obtained by adding aqueous ammonia to the reaction product.

The compounds of formula I and the salts thereof can be separated and purified by an ordinary manner, such as an extraction with an organic solvent, crystallization, column chromatography, etc.

Process 2:

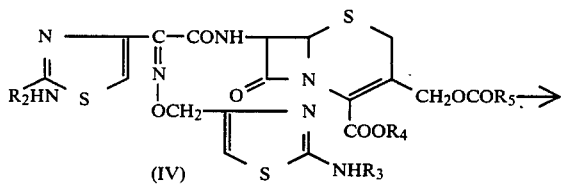

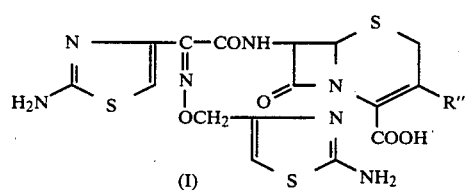

wherein R" represents the groups shown by R in the foregoing general formula I excluding a lower alkyl group which may be substituted by lower acyloxy group and a lower alkylthio group; $R_2$, $R_3$, and $R_4$ have the same significance as defined above; and $R_5$ represents a lower alkyl group.

The production process is a process of producing the desired compounds of formula I' by converting the lower acyloxy moiety of the 3-position of 7-{α-(2-amino-4-thiazolyl)-α-[(2-amino-4-thiazolyl)methoxyimino]acetamido}-3-(lower acyl)oxymethyl-3-cephem-4-carboxylic acid shown by formula IV into another group.

This reaction is usually performed by stirring a compound of formula IV or a salt thereof and a thiol compound or a pyridine compound constituting the substituent at a 3-position of the compound of formula I' in water or other inert solvent. Examples of the inert solvents used for the purpose are alcohols such as methanol, ethanol, etc.; amides such as dimethylformamide, acetamide, etc.; and acetones and acetonitrile.

For promoting the reaction, a catalyst such as potassium iodide, potassium bromide, sodium bromide, potassium thiocyanate, etc., may be added to the reaction system in an excessive amount. The reaction easily proceeds at room temperature or under heating.

In the other procedure, the 3-iodomethyl compound is

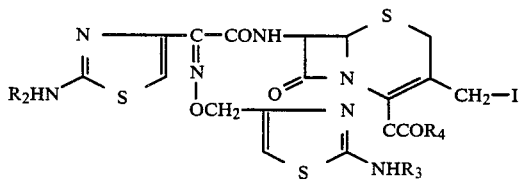

firstly obtained by reacting the compound (IV) (preferably protected by the silyl group) with trimethyl-silyl iodide (TMSI) in an inert solvent such as methylene chloride, chloroform, acetonitrile, acetone, etc. The solvent in the 3-iodomethyl compound containing solution is distilled away, the concentrate is dissolved in acetonitrile, and excess TMSI is decomposed by adding a small excess amount of tetrahydrofuran. To the solution thus formed is added the pyridine compound, etc. to provide the desired compound.

The reaction product can be converted into the salt thereof. Or, if desired, a protective group is removed. The removal of the protective group and the formation of the salt can be performed by the foregoing methods.

Then, the invention is further described by the following examples.

REFERENCE EXAMPLE (i) In 300 ml of ethanol was dissolved 25 g of 1,3-dichloro-2-propanone and after adding thereto 14,95 g of thiourea, the mixture was stirred for 2 hours at room temperature. The reaction mixture was concentrated and the residue was dissolved in 300 ml of dichloromethane. To the solution was added 54.2 g of chlorotriphenylmethane and after adding thereto 39.8 g of triethylamine under ice cooling, the mixture was stirred for 16 hours at room temperature. To the reaction mixture was added ice-water and the dichloromethane layer formed was separated, dried by anhydrous magnesium sulfate, and concentrated. The residue was applied to column chromatography and the product was first eluted with benzene and then a mixture of benzene and ethyl acetate (10:1) to provide 15 g of 4-chloromethyl-2-tritylaminothiazole.

NMR (DMSO-$d_6$): δ(ppm):

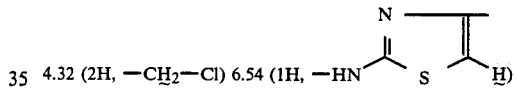

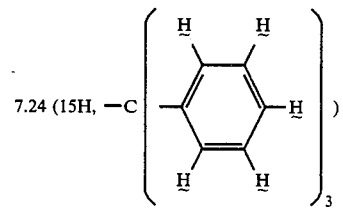

(ii) In 150 ml of acetonitrile was suspended 11.48 g of N-hydroxyphthalimide. To the suspension was added 7.11 g of triethylamine and dissoled therein. To the solution was added a solution of 27.5 g of 4-chloromethyl-2-tritylaminothiazole dissolved in 200 ml of dichloromethane and the mixture was stirred on an oil bath of 80° C. for 7 hours. The reaction mixture thus obtained was concentrated and the residue formed was dissolved in ethyl acetate. The solution was washed with water, dried by anhydrous magnesium sulfate, and concentrated. The residue was applied to column chromatography and the product was eluted with chloroform to provide 14.5 g of (2-tritylamino-4-thiazolyl)methoxyphthalimide.

NMR (DMSO-$d_6$): δ(ppm):

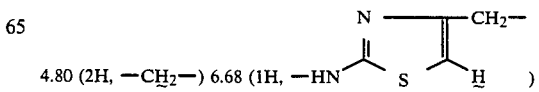

-continued 7.25 (15H, —C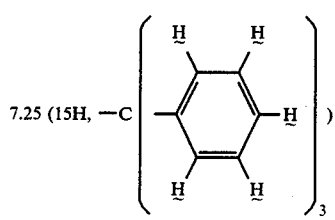)

7.83 (4H, 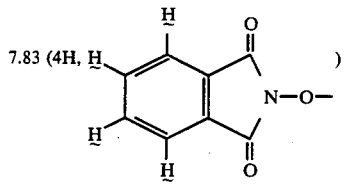)

(iii) In 80 ml of ethanol was suspended 6.2 g of (2-tritylamino-4-thiazolyl)methoxyphthalimide and after adding thereto 600 mg of hydrazine hydrate, the suspension was refluxed for 90 minutes. After cooling the reaction mixture by ice water, the precipitates thus formed were filtered and the filtrate was concentrated. To the residue was added 50 ml of ethyl acetate, insoluble materials precipitated were removed by filtration and the filtrate was concentrated. The residue thus formed was dissolved in 100 ml of ethanol. To the solution was added 4.78 g of 2-(2-tritylamino-4-thiazolyl)-glyoxylic acid and after further adding thereto 100 ml of methanol and 200 ml of dichloromethane, the mixture was stirred for one hour at room temperature. The reaction mixture was concentrated to ¼ of the original volume and 50 ml of dimethylformamide was added for dissolving the concentrate. The solution was stirred for 30 minutes and after adding thereto 500 ml of chloroform and 300 ml of ice water, the pH of the solution was adjusted to 1 to 2 with 1N hydrochloric acid solution. The precipitates thus formed were collected by filtration, were washed with water and then ether, and dried to provide 5.7 g of (Z)-α-(2-tritylamino-4-thiazolyl)-α-[(2-tritylamino-4-thiazolyl)methoxyimino]acetic acid. On the other hand, the chloroform layer thus formed was washed with water, dried by anhydrous magnesium sulfate, and concentrated. To the residue thus formed was added ether and the mixture was filtered to provide 0.51 g of the desired product.

NMR (DMSO-d$_6$): δ(ppm):

4.74 (2H, —CH$_2$—) 6.31, 6.76 (each 1H,

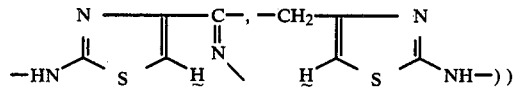

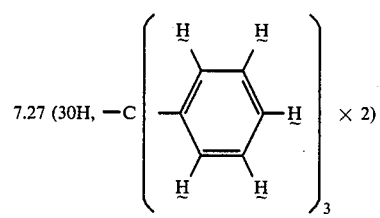

EXAMPLE 1

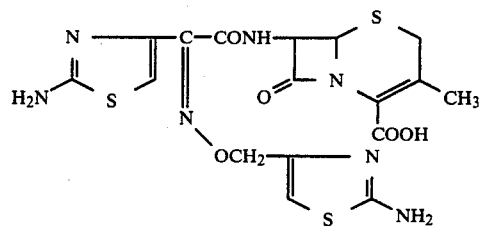

(a) In 8 ml of dichloromethane was suspended 626 mg of (Z)-α-(2-tritylamino-4-thiazolyl)-α[(2-tritylamino-4-thiazolyl)methoxyimino]acetic acid and after cooling the suspension to 3° to 4° C. and adding thereto 166 mg of phosphorus pentachloride, the mixture was stirred for 15 minutes at 3° to 4° C. to provide solution A. On the other hand, 304 mg of 7-amino-3-methyl-3-cephem-4-carboxylic acid benzhydryl ester was dissolved in 8 ml of dichloromethane and after cooling the solution to −40° C., 395 mg of pyridine was added to the solution to provide solution B. Solution A was added dropwise to solution B and the temperature of the mixture was increased to −20° C. over a period of 20 minutes. The reaction mixture was poured into 40 ml of ice water and after adjusting the pH thereof to 1 to 2 with 1N hydrochloric acid, the product was extracted with 150 ml of ethyl acetate. The ethyl acetate extract was washed with a saturated aqueous solution of sodium chloride, dried by anhydrous magnesium sulfate, and concentrated. The residue was applied to silica gel column chromatography and the product was first eluted with benzene and then with a mixture of benzene and ethyl acetate (4:1) to provide 710 mg of (Z)-7-{α-(2-tritylamino-4-thiazolyl)-α-[(2-tritylamino-4-thiazolyl)methoxyimino]acetamido}-3-methyl-3-cephem-4-carboxylic acid benzhydryl ester.

NMR (DMSO-d$_6$): δ(ppm):

1.98 (3H, —CH$_3$)

3.42 (2H, 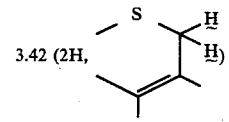)

4.78 (2H, 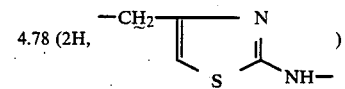)

5.10 (1H, 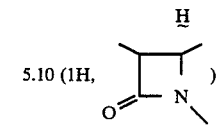)

5.68 (1H, 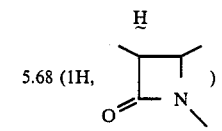)

-continued 6.39, 6.71 (each 1H, 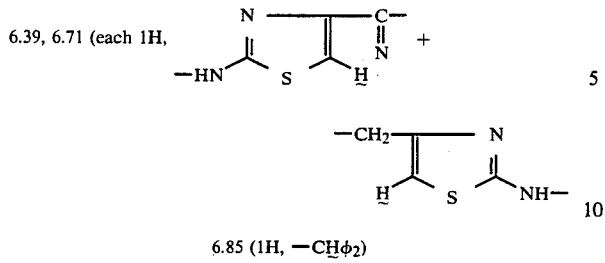 +

6.85 (1H, —CH$\phi_2$)

7.04~7.60  40H, —C(C$_6$H$_5$)$_3$ × 2 + —CH(C$_6$H$_5$)$_2$ (b) In 4 ml of dichloromethane was dissolved 0.71 g of (Z)-7-{α-(2-tritylamino-4-thiazolyl)-α-[(2-tritylamino-4-thiazolyl)methoxyimino]acetamido}-3-methyl-3-cephem-4-carboxylic acid benzhydryl ester and after adding thereto 0.4 ml of anisole and then 4 ml of trifluoroacetic acid under ice-cooling, the mixture was stirred for 20 minutes. The reaction mixture was concentrated and 20 ml of ether and 20 ml of petroleum ether were added thereto to cause solidification. The solid product was filtered, dried, ice-cooled, and dissolved in 8 ml of trifluoroacetic acid. After adding 2.5 ml of water to the solution, the mixture was stirred for one hour at 22° to 23° C. The reaction mixture was concentrated and the residue was dissolved in 0.5 ml of ethanol. Then, 30 ml of ether was added to the solution and precipitates thus formed were collected by filtration, washed with ether, and dried to provide 260 mg of the powder of the ditrifluoroacetate (ditrifluoroacetic acid salt) of (Z)-7-{α-(2-amino-4-thiazolyl)-α-[(2-amino-4-thiazolyl)methoxyimino]acetamido}-3-methyl-3-cephem-4-carboxylic acid.

NMR (DMSO-d$_6$): δ(ppm):

2.03 (3H, —CH$_3$) 3.42 (2H, 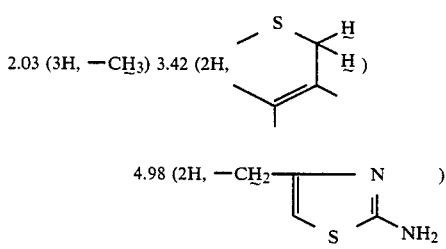

4.98 (2H, —CH$_2$—C(=N)—S—NH$_2$ )

-continued 5.08 (1H, ) 5.68 (1H, ) 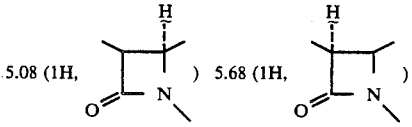

6.83, 6.86 (each 1H, H$_2$N— 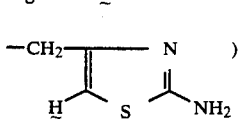 +

—CH$_2$—C(=N)—S—NH$_2$ )

EXAMPLE 2

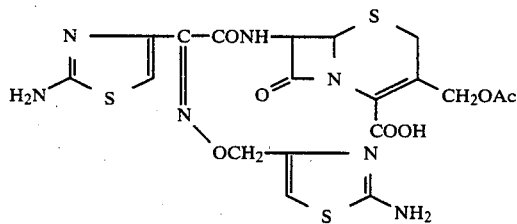

(a) In 12 ml of dichloromethane was suspended 1.566 g of (Z)-α-(2-tritylamino-4-thiazolyl)-α-[(2-tritylamino-4-thiazolyl)methoxyimino]acetic acid and after cooling the suspension to 3° to 4° C. and adding thereto 416 mg of phosphorus pentachloride, the mixture was stirred for 15 minutes at 3° to 4° C. to provide solution A. On the other hand, 844 mg of 7-amino-3-acetoxymethyl-3-cephem-4-carboxylic acid benzhydryl ester was dissolved in 20 ml of dichloromethane and after cooling the solution to −40° C., 1 g of pyridine was added thereto to provide solution B. Solution A was added dropwise to solution B and the temperature was increased up to −10° C. over a period of 30 minutes. The reaction mixture was poured in 50 ml of ice water and after adjusting the pH thereof to 1 to 2 with 1N hydrochloric acid, the product was extracted with 150 ml of ethyl acetate. The ethyl acetate extract thus obtained was washed with water, dried with anhydrous magnesium sulfate, and concentrated. The residue was applied to silica gel column chromatography and the product was first eluted with benzene and then a mixture of benzene and ethyl acetate (4:1) and further benzene and ethyl acetate (2:1) to provide 1 g of (Z)-7-{α-(2-tritylamino-4-thiazolyl)-α-[(2-tritylamino-4-thiazolyl)methoxyimino]acetoamido}-3-acetoxymethyl-3-cephem-4-carboxylic acid benzhydryl ester.

(b) In 4 ml of dichloromethane was dissolved 1 g of (Z)-7-{α-(2-tritylamino-4-thiazolyl)-α-[(2-tritylamino-4-thaizolyl)methoxyimino]acetamido}-3-acetoxymethyl-3-cephem-4-carboxylic acid benzhydryl ester and after adding 0.5 ml of anisole under ice-cooling and then adding 4 ml of trifuoroacetic acid, the resultant mixture was stirred for 20 minutes. The reaction mixture was concentrated and 30 ml of ether and 10 ml of petroleum ether were added to the concentrate to cause solidification. The solids thus formed were collected by filtration, dried, and then dissolved in 16 ml of trifluoroacetic acid under ice-cooling. Then, 6 ml of water was added to the solution and the mixture was stirred for one hour at 20°–23° C. The reaction mixture was concentrated, the residue thus formed was dissolved in 0.5 ml of ethanol and 20 ml of ether was added to the solution to form precipitates, which were collected by filtration, washed with ether, and dried to provide 0.5 g of a ditrifluoroacetate (ditrifluoroacetic acid salt) of (Z)-7-{α-(2-amino-4-thiazolyl)-α-[(2-amino-4-thiazolyl)methoxyimino]acetamido}-3-acetoxymethyl-3-cephem-4-carboxylic acid.

NMR (DMSO-d$_6$): δ(ppm):

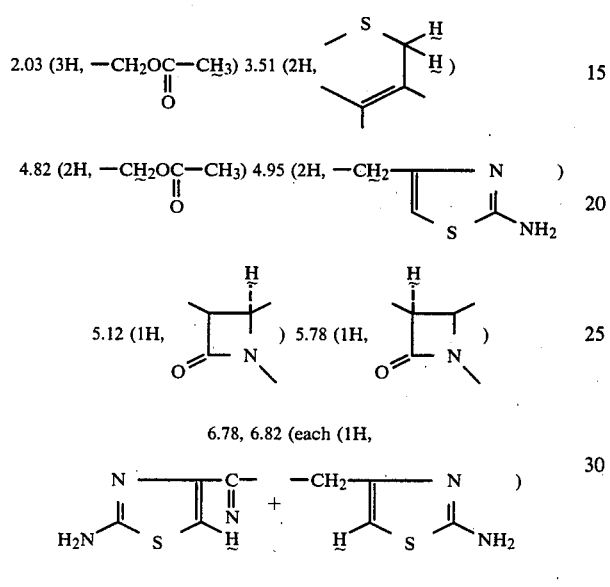

EXAMPLE 3

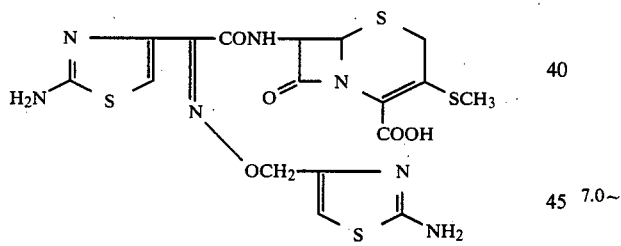

(a) In 8 ml of dichloromethane was suspended 630 mg of (Z)-α-(2-tritylamino-4-thiazolyl)-α-[(2-tritylamino-4-thiazolyl)methoxyimino]acetic acid and after cooling the suspension to 3°–4° C. and adding thereto 170 mg of phosphorus pentachloride, the mixture was stirred for 15 minutes at 3°–4° C. to provide solution A.

On the other hand, 330 mg of 7-amino-3-methylthio-3-cephem-4-carboxylic acid benzhydryl ester was dissolved in 8 ml of dichloromethane and after cooling the solution to −40° C., 0.5 ml of pyridine was added to the solution to provide solution B.

After adding dropwise solution A to solution B, the temperature of the mixture was increased to −20° C. over a period of 30 minutes. The reaction mixture was poured to 50 ml of ice water and after adjusting the pH of the system to 1 to 2 with 1N hydrochloric acid, the product was extracted with 100 ml dichloromethane. The dichloromethane extract was washed with a saturated aqueous sodium chloride solution, dried by anhydrous magnesium sulfate, and concentrated. The residue thus formed was applied to silica gel column chromatography and the product was first eluted with benzene and then with a mixture of benzene and ethyl acetate (9:1) to provide 600 mg of (Z)-7-{α-(2-tritylamino-4-thiazolyl)-α-[(2-tritylamino-4-thiazolyl)methoxyimino]acetamido}-3-methylthio-3-cephem-4-carboxylic acid benzhydryl ester.

NMR (CDCl$_3$): δ(ppm):

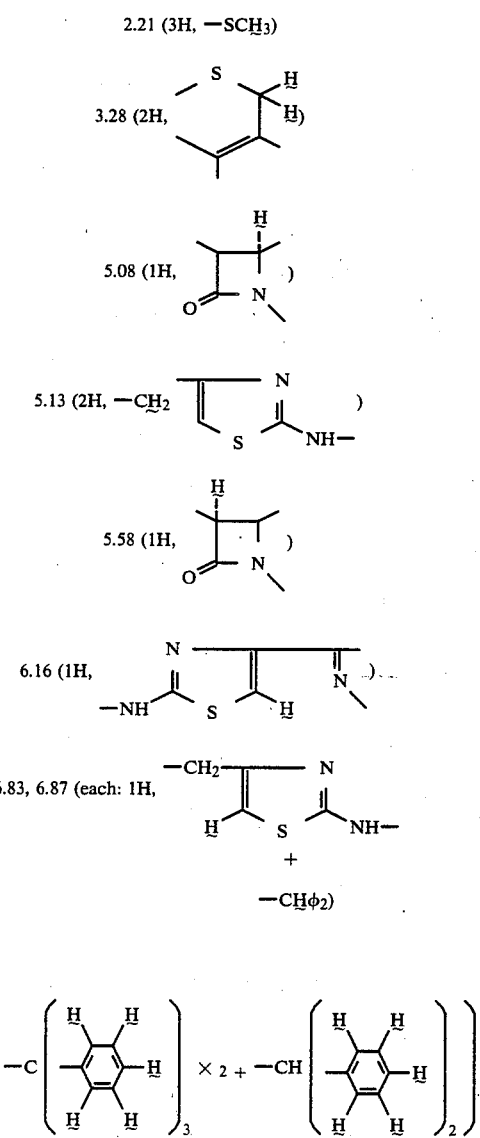

(b) 0.5 ml of anisole was added to 600 mg (Z)-7-{α-(2-tritylamino-4-thiazolyl)-α-[(2-tritylamino-4-thiazolyl)methoxyimino]acetamido}-3-methylthio-3-cephem-4-carboxylic acid benzhydryl ester and after adding 10 ml of trifluoroacetic acid to the mixture under ice-cooling, the mixture was stirred for 20 minutes. 5 ml of water was added to the mixture and the resultant mixture was stirred for one hour at room temperature. The reaction mixture was concentrated and the residue was mixed with 30 ml of ethyl ether and powdered. The powder thus obtained was collected by filtration, washed with ether, and dried to give 300 mg of the powder of the ditrifluoroacetate of (Z)-7-{α-(2-amino-4-thiazolyl)-α-[(2-amino-4-thiazolyl)methoxyimino]acetamido}-3-methylthio-3-cephem-4-carboxylic acid.

NMR (DMSO-d₆): δ(ppm):

2.35 (3H, —SCH₃)

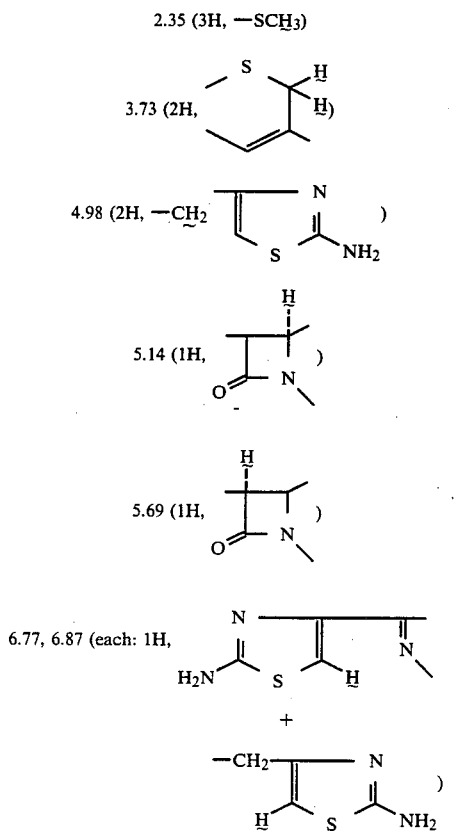

3.73 (2H, )

4.98 (2H, —CH₂ )

5.14 (1H, )

5.69 (1H, )

6.77, 6.87 (each: 1H, )

+

—CH₂— )

EXAMPLE 4

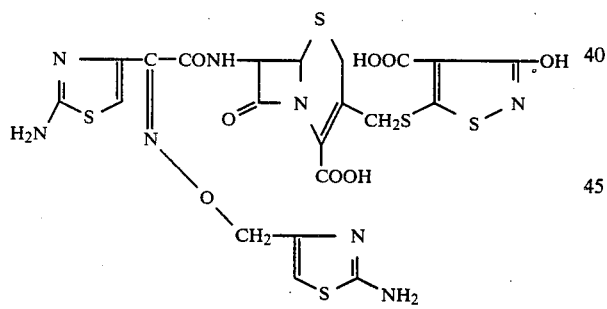

(a) In 40 ml of 1,4-dioxane were suspended 3.91 g of (Z)-α-(2-tritylamino-4-thiazolyl)-α-[(2-tritylamino-4-thiazolyl)methoxyimino]acetic acid and 0.742 g of 1-hydroxybenztriazole. To the solution was added 1.13 g of N,N-dicyclohexylcarbodiimide and the mixture was reacted for one hour at room temperature. After the reaction was over, dicyclohexylurea thus precipitated was filtered away to provide a dioxane solution of active ester. On the other hand, 1.75 g of 7-amino-3-[(4-carboxy-3-hydroxy-5-isothiazolyl)thiomethyl]-3-cephem-4-carboxylic acid was suspended in 17 ml of N,N-dimethylformamide and after adding thereto 1.26 ml of triethylamine, the mixture was stirred for 60 minutes at room temperature. To the brown solution thus obtained was added dropwise the dioxane solution of the active ester obtained in the foregoing process and the mixture was reacted for one night at room temperature. The reaction mixture was distilled under reduced pressure to remove 1,4-dioxane and after adding to the residue obtained 20 ml of water and 5 ml of a saturated sodium hydrogen carbonate solution, the resultant solution was extracted with 100 ml of ethyl acetate and then 50 ml of ethyl acetate in order to wash the solution. The aqueous layer thus obtained was acidified by the addition of 10 ml of 2N-hydrochloric acid and extracted with 100 ml of a mixture of methyl ethyl ketone and ethyl acetate (1:1 by volume ratio) and then 50 ml of the mixture having the same composition. Unreacted raw materials precipitated during procedure were removed by filtration. The extract was washed once with 30 ml of water and then twice each time with 30 ml of a saturated sodium chloride solution and after drying by anhydrous magnesium sulfate, were removed ethyl acetate and methyl ethyl ketone under reduced pressure to provide a carmel. The caramel was applied to silica gel column chromatography and eluted with a mixture of chloroform, isopropyl alcohol, and formic acid (90:10:2 by volume ratio). The fractions containing the desired product were collected, the solvent was distilled off, and the residue was powdered with ether to provide 610 mg of (Z)-7-{α-(2-tritylamino-4-thiazolyl)-α-[(2-tritylamino-4-thiazolyl)methoxyimino]acetamido}-3-[(4-carboxy-3-hydroxy-5-isothiazolyl)thiomethyl]-3-cephem-4-carboxylic acid.

Infrared absorption spectra $\nu_{max}^{KBr}$ cm⁻¹: 3400–3300, 3040, 2920, 1775, 1685–1670, 1510–1520, 1490, 1440, 995, 895, 750, and 695.

NMR (CDCl₃): δ(ppm):

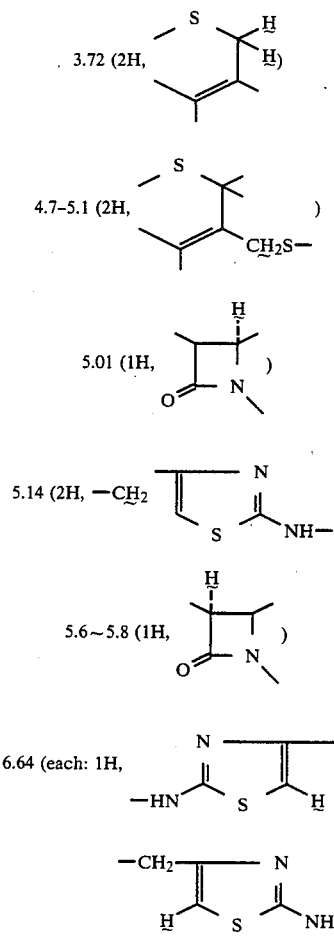

3.72 (2H, )

4.7–5.1 (2H, )

5.01 (1H, )

5.14 (2H, —CH₂ )

5.6–5.8 (1H, )

6.20, 6.64 (each: 1H, )

-continued 6.8~7.5 (30H, 6φ)

(b) After cooling 10 ml of trifluoroacetic acid to 15° C., 600 mg of (Z)-7-{α-(2-tritylamino-4-thiazolyl)-α-[(2-tritylamino-4-thiazolyl)methoxyimino]acetamido}-3-[(4-carboxy-3-hydroxy-5-isothiazolyl)thiomethyl]-3-cephem-4-carboxylic acid was added thereto to dissolve it. To the solution was added 5 ml of water at temperatures below 20° C. and then the reaction was performed for 3 hours at 19°–21° C. After the reaction was over, the reaction mixture was concentrated under reduced pressure and the residue was dissolved in 20 ml of ethanol and then ethanol and water were distilled off again. The residue thus formed was dissolved in 0.5 ml of ethanol and 20 ml of ether was added to the solution to form precipitates, which were collected by filtration, washed with 20 ml of ether, and dried to provide 264 mg of (Z)-7-{(2-amino-4-thiazolyl)-α-[(2-amino-4-thiazolyl)mthoxyimino]-acetamido}-3-[(4-carboxy-3-hydroxy-5-isothiazolyl)-thiomethyl]-Δ³-cephem-4-carboxylic acid trifluoroacetate.

Infrared absorption spectra $\nu_{max}^{KBr}\text{cm}^{-1}$: 3300–3250, 3100–3060, 1770, 1670–1620, 1190, 1130, 1020, 830, 795, and 720.

NMR (DMSO-d₆): δ(ppm):

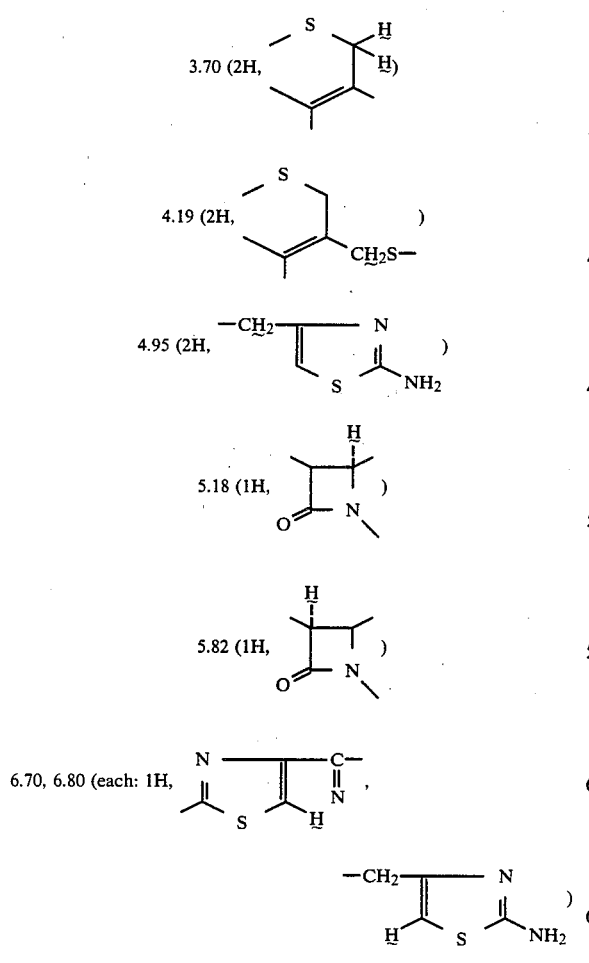

(c)

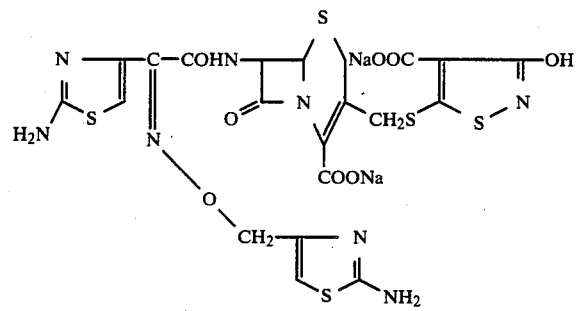

In 5 ml of water was suspended 260 mg of the foregoing trifluoroacetate and 70 mg of sodium hydrogencarbonate was added to dissolve. The product thus produced was adsorbed on Diaion HP-20 (made by Mitsubishi Chemical Industries Ltd.). Then, the product was first eluted with 300 ml of water and then a mixture of water and methanol (9:1 by volume ratio). The fractions containing the desired product was concentrated, and lyophilized to provide 76 mg of disodium (Z)-7-{α-(2-amino-4-thiazolyl)-α-[(2-amino-4-thiazolyl)methoxyimino]acetamido}-3-[(4-carboxylate-3-hydroxy-5-isothiazolyl)thiomethyl]-3-cephem-4-carboxylate.

Infrared absorption spectra: $\nu_{max}^{KBr}\text{cm}^{-1}$: 3430–3360, 1760, 1615, 1520, 1350, and 1005.

NMR (D₂O): δ(ppm):

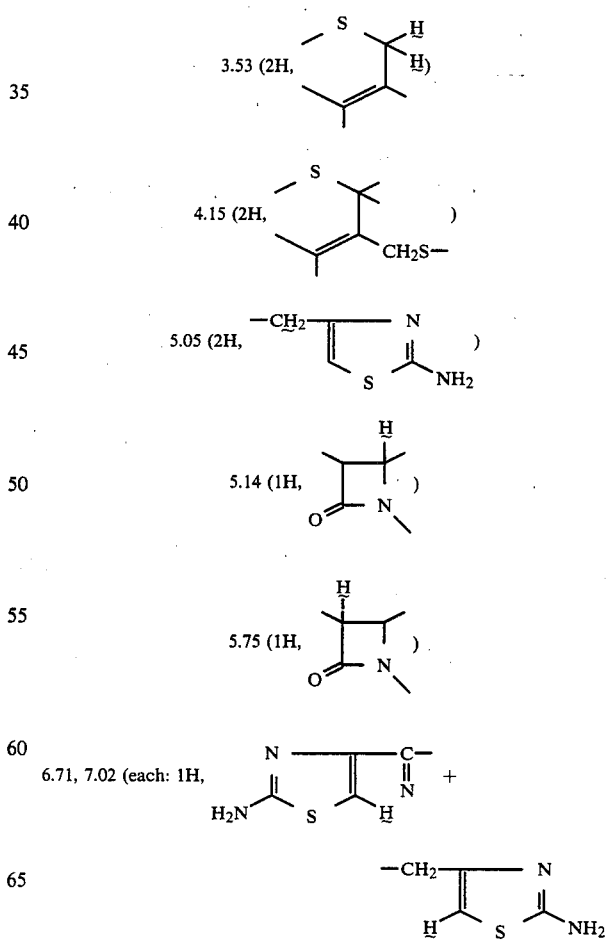

EXAMPLE 5

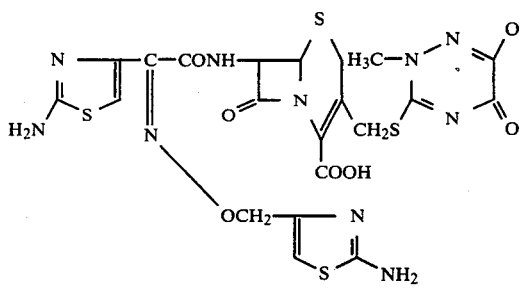

In 4 ml of water was stirred 220 mg of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid together with 95 mg of 2,5-dihydro-6-hydroxy-2-methyl-5-oxo-3-mercaptotriazine and 142 mg of sodium hydrogen carbonate for 14 hours at 55° C. The reaction mixture was cooled to 10° C. and the pH of the solution was adjusted to 1 to 2 with 1N-hydrochloric acid to form precipitates. To the precipitates was added 20 ml of a mixture of n-butanol and ethyl acetate (1:1) followed by stirring and the precipitates formed were collected by filtration, washed with water and ether, and dried to provide 110 mg of a powder of (Z)-7-{α-(2-amino-4-thiazolyl)-α-[(2-amino-4-thiazolyl)methoxyimino]acetamido}-3-{[(2,5-dihydro-6-hydroxy-2-methyl-5-oxo-as-triazine-3-yl)thio]methyl}-3-cephem-4-carboxylic acid.

NMR (DMSO-$d_6$): δ(ppm):

3.58 (3H, 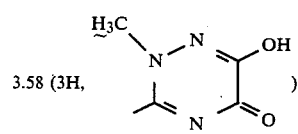 )

3.65 (2H, 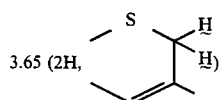 )

4.22 (2H, 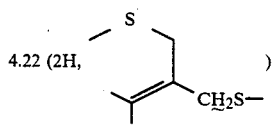 )

4.88 (2H, 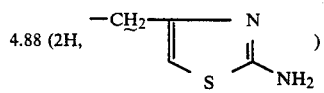 )

5.12 (1H, 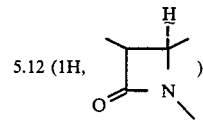 )

5.76 (1H, 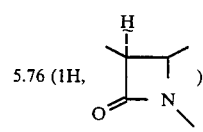 )

6.41, 6.71 (each: 1H, 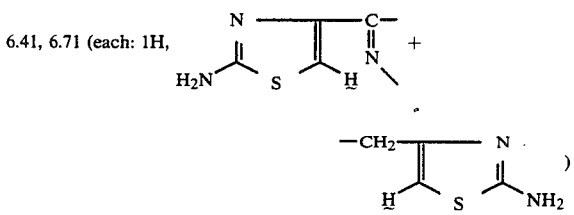 )

EXAMPLE 6

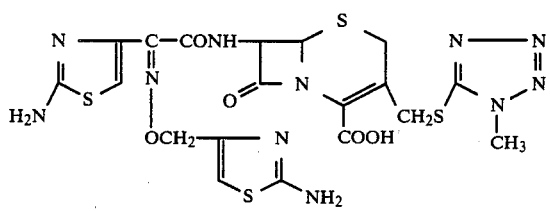

(a) In 6 ml of dichloromethane was suspended 500 mg of (Z)-α-(2-tritylamino-4-thiazolyl)-α-[(2-tritylamino-4-thiazolyl)methoxyimino]acetic acid and after cooling the suspension to 3°–4° C. and adding thereto 133 mg of phosphorus pentachloride, the mixture was stirred for 15 minutes at 3°–4° C. On the other hand, 316 mg of 7-amino-3-(1-methyl-5-tetrazolyl)thiomethyl-3-cephem-4-carboxylic acid benzhydryl ester was dissolved in 6 ml of dichloromethane. After cooling the solution to −35° C. and adding 500 mg of pyridine, the foregoing dichloromethane solution containing acid chloride was added dropwise to the solution. Thereafter, the mixture was stirred for 15 minutes at −20° C. to −30° C., 20 ml of ice water was added to the reaction solution, the pH of the solution was adjusted to 1-2 with 1N hydrochloric acid, and the dichloromethane layer thus formed was separated. The dichloromethane layer was washed with water, dried (over anhydrous magnesium sulfate), and concentrated. The residue thus formed was applied to column chromatography and it was eluted with benzene and then with a mixture of benzene and ethyl acetate (5:1) to provide 510 mg of (Z)-7-{α-(2-tritylamino-4-thiazolyl)-α-[(2-tritylamino-4-thiazolyl)methoxyimino]acetamido}-3-[(1-methyl-5-tetrazolyl)thiomethyl]-3-cephem-4-carboxylic acid benzhydryl ester.

NMR (DMSO-$d_6$): δ(ppm):

3.68 (2H, 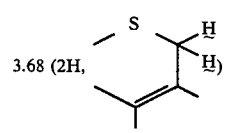 )

3.85 (3H, 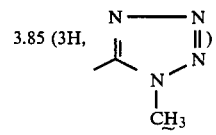 )

4.26 (2H, 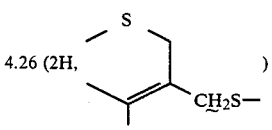 )

-continued 4.98 (2H, N(=O)–O–CH₂–)

5.14 (1H, CH–C(=O)–N)

5.78 (1H, CH–C(=O)–N)

6.38, 6.70 (each: 1H,
(–HN–S–CH=C(N)–C(=N)– + –CH₂–C(=N)(S–CH=)–NH–))

6.86 (1H, –CHφ₂)

7.29 {40H, [–C(C₆H₅)₃]×2 + [–CH(C₆H₅)₂]}

(b) In 4 ml of dichloromethane was dissolved 510 mg of (Z)-7-{α-(2-tritylamino-4-thiazolyl)-α-[(2-tritylamino-4-thiazolyl)methoxyimino]acetamido}-3-[(1-methyl-5-tetrazolyl)thiomethyl]-3-cephem-4-carboxylic acid benzhydryl ester and after adding thereto 0.5 ml of anisole and 4 ml of trifluoroacetic acid under ice-cooling, the mixture was stirred for 20 minites. The reaction mixture was concentrated and 30 ml of ether was added to cause solidification. The solids were collected by filtration, dried, dissolved in 6 ml of trifluoroacetic acid under ice-cooling and then 3 ml of water was added to the solution. The solution was stirred for one hour at 20°–23° C. and the solution was concentratred. The residue thus formed was dissolved in 0.4 ml of ethanol and the solution was mixed with ether to form precipitates, which were collected by fitration and washed with ether and dried to provide 200 mg of a powder of (Z)-{α-(2-amino-4-thiazolyl)-α-[(2-amino-4-thiazolyl)methoxyimino]acetamido}-3-[(1-methyl-5-tetrazolyl)thiomethyl]-3-cephem-4-carboxylic acid.

NMR (DMSO-d₆): δ(ppm):

3.68 (2H, S–CH₂–C=C(CH₃))

3.94 (3H, N=N–N(CH₃)–N=C–CH₃)

4.31 (2H, S–CH₂–C=C(CH₃)–CH₂S–)

4.96 (2H, N(=O)–OCH₂–)

5.12 (1H, CH–C(=O)–N)

5.78 (1H, CH–C(=O)–N)

6.74, 6.81 (each: 1H,
(H₂N–S–CH=C(N)–C(=N)– + –CH₂–C(=N)(S–CH=)–NH₂))

EXAMPLE 7

[structure of cephalosporin with 2-aminothiazolyl, methoxyimino, pyridazinium groups, COO⁻]

In 7 ml of water were dissolved 7.48 g of sodium iodide, 252 mg of sodium hydrogencarbonate, 1.2 g of pyridazine, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred at 60°–65° C. for 10 hours.

The reaction mixture was cooled, applied to column chromatography containing Diaion HP-20 (made by Mitsubishi Chemical Industries Ltd.), and the product was first eluted with water and then with mixtures of water and methanol while changing the mixing ratio successively. The fractions containing the desired material were collected, concentrated, and lyophylized to provide 62 mg of (Z)-7-{α-(2-amino-4-thiazolyl)-α-[(2-amino-4-thiazolyl)methoxyimino]acetamido}-3-(1-pyridadiniomethyl)-3-cephem-4-carboxylate.

NMR (DMSO-d₆): δ(ppm):

4.90 (2H, 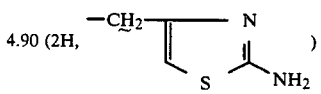 )

5.06 (1H, 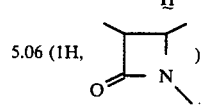 )

5.76 (1H, 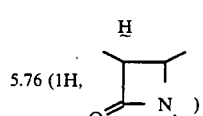 )

6.45, 6.74 (each: 1H, 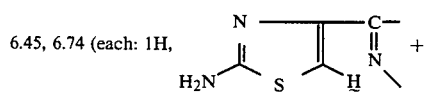 +

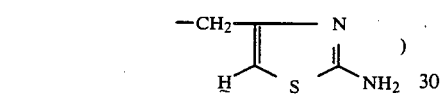 )

8.70 (2H, 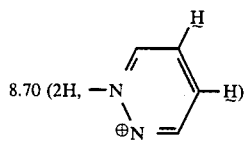 )

9.58 (1H, 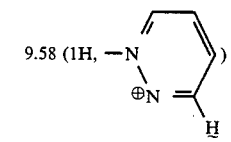 )

10.29 (1H, 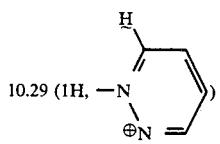 )

EXAMPLE 8

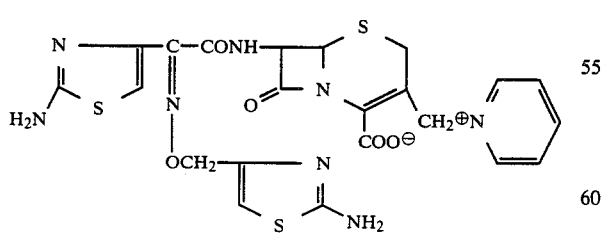

In 0.6 ml of water was suspended 1.98 g of sodium iodide and after adding thereto 0.5 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and 0.56 ml of pyridine, the mixture was stirred on an oil bath of 80° C. for one hour.

The reaction mixture was concentrated, 25 ml of water was added to the residue formed, and after adjusting the pH of the mixture to about 1 with 1N hydrochloric acid, insoluble materials were removed by filtration. The pH of the filtrate was adjusted to about 6.5 with sodium hydrogencarbonate, the filtrate was adsorbed on Diaion HP-20 (made by MItsubishi Chemical Industries Ltd). Then, the product was eluted first with water and then with mixed solutions of water and methanol (successively changing the mixing ratio from 100:5 to 100:200). The fractions containing the desired product were collected, concentrated, and lyophilized to provide 60 mg of (Z)-7-{α-(2-amino-4-thiazolyl)-α-[(2-amino-4-thiazolyl)methoxyimino]acetamido}-3-(1-pyridiniummethyl)-3-cephem-4-carboxylate.

NMR (DMSO-d₆): δ(ppm):

4.88 (2H, 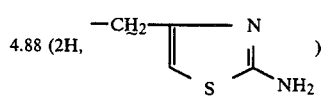 )

5.08 (1H, 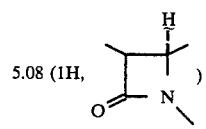 )

5.72 (1H, 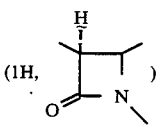 )

6.40, 6.68 (each: 1H, 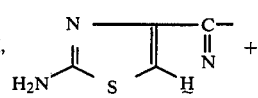 +

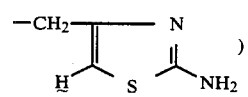 )

8.13 (2H, 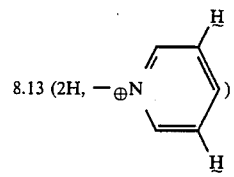 )

8.57 (1H, 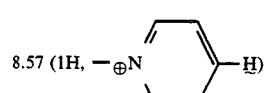 )

9.39 (2H, 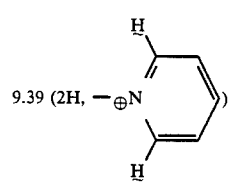 )

EXAMPLE 9

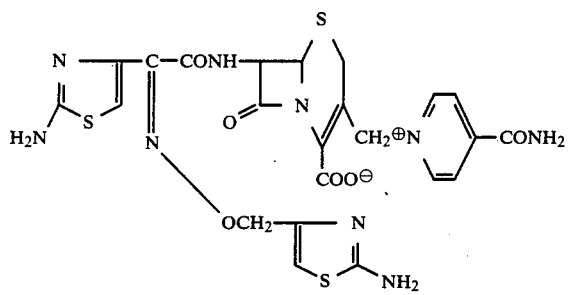

In 7 ml of water were dissolved 7.47 g of potassium iodide, 138 mg of sodium hydrogencarbonate, 1.83 g of isonicotinamide, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for one hour at 53° C. Thereafter, 25 mg of sodium hydrogen-carbonate was added to the mixture and the resultant mixture was further stirred for 4 hours at the same temperature. The reaction mixture was cooled, adsorbed on Diaion HP-20 (made by Mitsubishi Chemical Industries Ltd.), eluted first with water, and then with mixed solutions of water and methanol (successively changing the mixing ratio from 100:5 to 100:200), and the fractions containing the desired product were collected, concentrated, and then lyophilized. The lyophilized product was dissolved in water and the solution was adsorbed again on Diaion HP-20 to purify it by repeating the same procedure as above to provide 90 mg of (Z)-7-{α-(2-amino-4-thiazolyl)-α-[(2-amino-4-thiazolyl)methoxyimino]acetamido}-3-(4-carbamoyl-1-pyridiniummethyl)-3-cephem-4-carboxylate.

NMR (DMSO-d$_6$): δ(ppm):

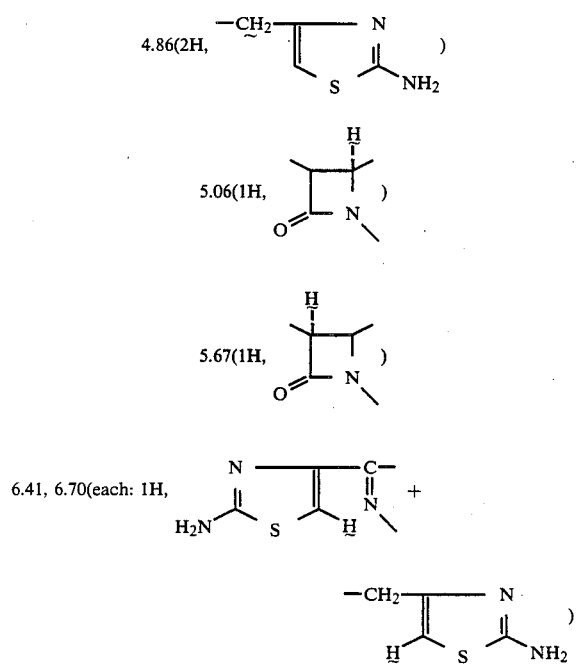

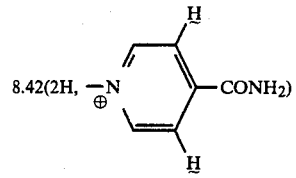

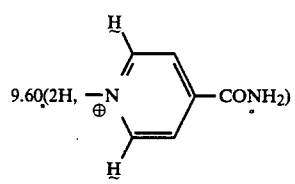

EXAMPLE 10

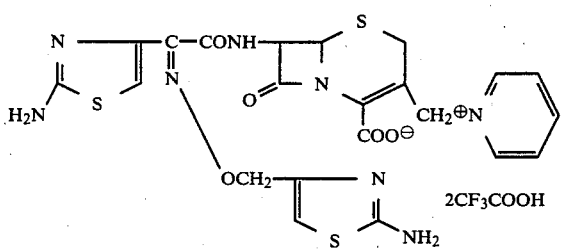

In 5 ml of dichloromethane was suspended 783 mg of (Z)-α-(2-tritylamino-4-thiazolyl)-α-[(2-tritylamino-4-thiazolyl)methoxyimino]acetic acid and after cooling the suspension to 3° to 4° C. and adding thereto 220 mg of phosphorus pentachloride, the mixture was stirred for 15 minutes at the same temperature to provide solution A. On the other hand, in 7 ml of tetrahydrofuran was suspended 364 mg of 7-amino-3-(1-pyridiniummethyl)-3-cephem-4-carboxylate dihydrochloride, 1.19 g of N-trimethylsilylacetamide was added to the suspension, and after stirring the mixture for 20 minutes at 35°-40° C. and cooling the mixture to −30° C., 0.5 ml of pyridine was added to the mixture to provide solution B.

Solution A was added to solution B at a temperature of −30° C. to −20° C. and then the temperature of the reaction mixture was increased up to −15° C. After adding to the reaction mixture 1 ml of water, the mixture was concentrated. To the residue thus formed was added 30 ml of ice water and the precipitates thus formed were collected by filtration, washed with water, and dried to provide 1.05 g of solid products. Then, 1.05 g of the solids were dissolved in 6 ml of trifluoroacetic acid under ice-cooling and after adding 2 ml of water to the solution, the mixture was stirred for one hour at 20° to 23° C. The reaction mixture thus obtained was concentrated and the residue formed was mixed with 30 ml of ether to form precipitates, which were collected by filtration, washed with ether, and dried to provide 550 mg of the powder of (Z)-{α-(2-amino-4-thiazolyl)-α-[(2-amino-4-thiazolyl)methoxyimino]acetamido}-3-(1-pyridiniummethyl)-3-cephem-4-carboxylate ditrifluoroacetate.

NMR (DMSO-d$_6$): δ(ppm):

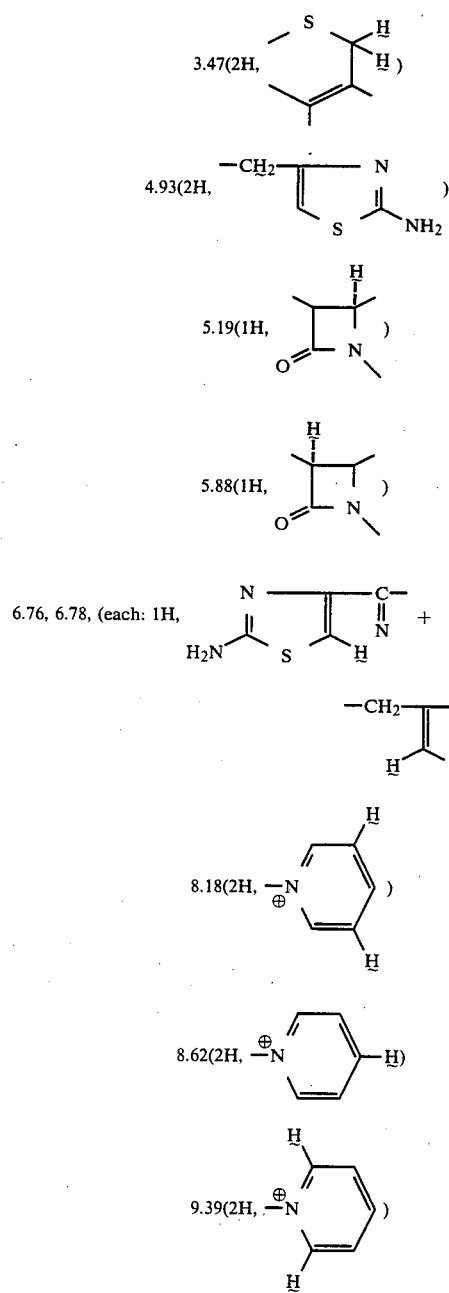

fluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 5 hours at 56°–58° C. The reaction mixture was cooled and adsorbed on Diaion HP-20 (made by Mitsubishi Chemical Industries Ltd.). The product was eluted first with water and then with mixtures of water and methanol (successively changing the mixing ratio from 10:1 to 10:6) and the fractions containing the desired product were collected, concentrated, and then lyophilized to provide 130 mg of a soidum salt of (Z)-7-{α-(2-amino-4-thiazolyl)-α-[(2-amino-4-thiazolyl)methoxyimino]acetoamido}-3-(4-β-sulfoethylpyridinium)-methyl-3-cephem-4-carboxylic acid.

NMR (DMSO-d$_6$): δ(ppm):

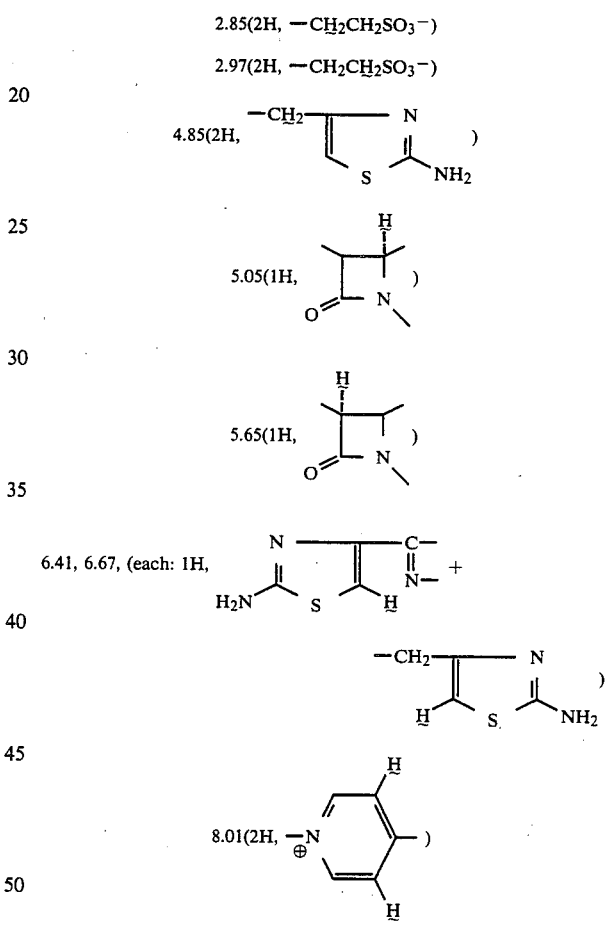

EXAMPLE 11

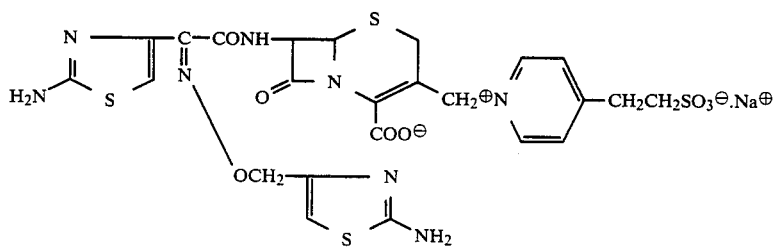

In 7 ml of water were dissolved 7.48 g of potassium iodide, 1.26 g of sodium hydrogencarbonate, 2.80 g of 4-pyridineethanesulfonic acid, and 1.087 g of a ditri- -continued 9.25(2H, 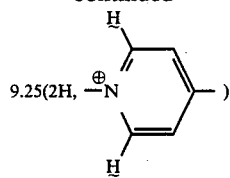)

EXAMPLE 12

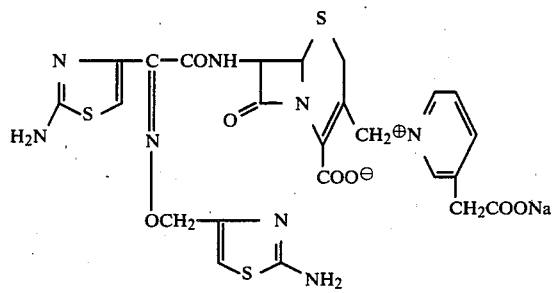

In 7 ml of water were dissolved 7.48 g of potassium iodide, 1.26 g of sodium hydrogencarbonate, 2.55 g of 3-pyridineacetic acid, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C. The reaction mixture was cooled and applied to column chromatography of Diaion HP-20 (made by Mitsubishi Chemical Industries Ltd.) The product was eluted first with water and then with mixtures of water and methanol while successively changing the mixing ratio thereof and the fractions containing the desired product were collected, concentrated, and lyophilized to provide 124 mg of (Z)-7-{α-(2-amino-4-thiazolyl)-α-[(2-amino-4-thiazolyl)methoxyimino]acetamido}-3-(3-carboxylate methyl-1-pyridiniomethyl)-3-cephem-4-carboxylate mono-sodium salt.

NMR (DMSO-d$_6$): δ(ppm):

3.91, (2H, —CH$_2$COO$^-$)

4.86(2H, 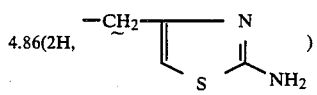)

5.07(1H, 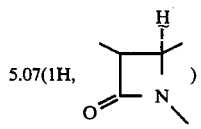)

5.68(1H, 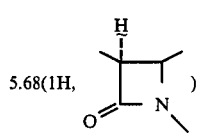)

6.40, 6.68(each: 1H, 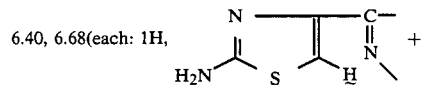)

-continued

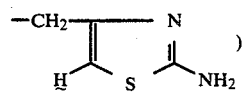

8.10(1H, 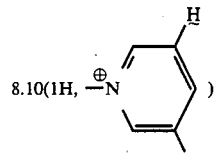)

8.49(1H, 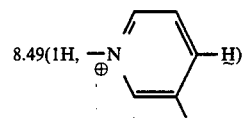)

9.25(1H, 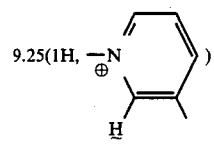)

9.41(1H, 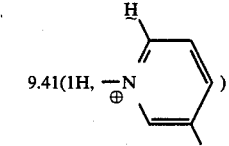)

EXAMPLE 13

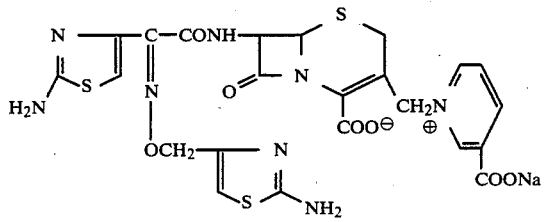

In 7 ml of water were dissolved 7.48 g of potassium iodide, 1.26 g of sodium hydrogencarbonate, 1.845 g of 3-pyridinecarboxylic acid, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C.

The reaction mixture was cooled and was applied to column chromatography of Diaion HP-20 and the product was eluted first with water and then with mixtures of water and methanol while changing succesively the mixing ratio. The fractions containing the desired product were collected, concentrated, and lyophilized to provide 95 mg of (Z)-7-{α-(2-amino-4-thiazolyl)-α-[(2-amino-4-thiazolyl)methoxyimino]acetamido}-3-(3-carboxylate-1-pyridiniomethyl)-3-cephem-4-carboxylate mono-sodium salt.

NMR (DMSO-d$_6$): δ(ppm):

4.86(2H, 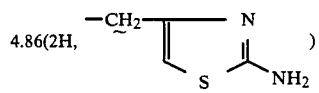)

-continued 5.13(1H, 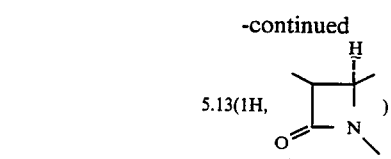)

5.77(1H, 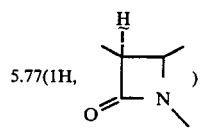)

6.40, 6.69(each: 1H, 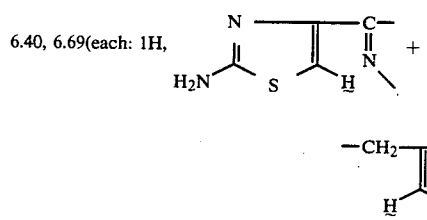 +

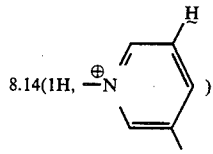)

8.14(1H, 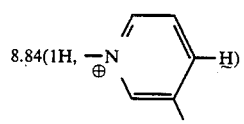)

8.84(1H, 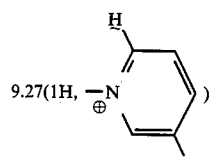)

9.27(1H, 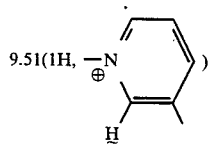)

9.51(1H, 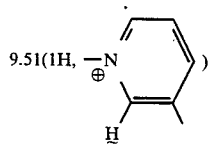)

EXAMPLE 14

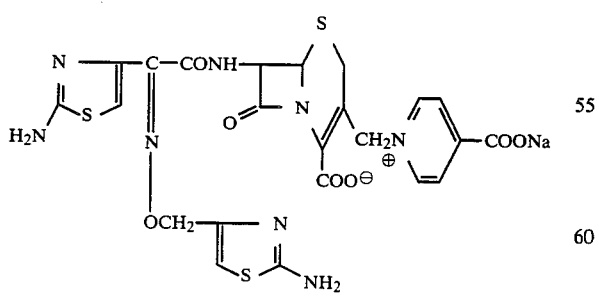

In 7 ml of water were dissolved 7.48 g of potassium iodide, 1.26 g of sodium hydrogencarbonate, 1.845 g of 4-pyridinecarboxylic acid, and 1.087 g of a ditrifuloroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C.

The reaction mixture was cooled and applied to colum chromatography of Diaion HP-20. The product was eluted first with water and then with mixtures of water and methanol while successively changing the mixing ratio thereof. The fractions containing the desired product were collected, concentrated, and lyophilized followed by drying to provide 85 mg of (Z)-7-{α-(2-amino-4-thiazolyl)-α-[(2-amino-4-thiazolyl)methoxyimino]acetamido}-3-(4-carboxylate-1-pyridiniomethyl)-3-cephem-4-carboxylate mono-sodium salt.

NMR (DMSO-d₆): δ(ppm):

4.87(2H, 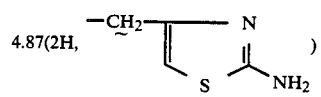)

5.13(1H, 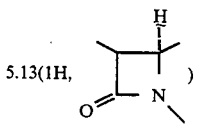)

5.78(1H, 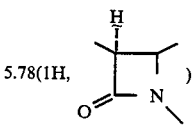)

6.40, 6.69(each: 1H, 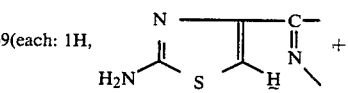 +

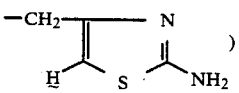)

8.29(2H, 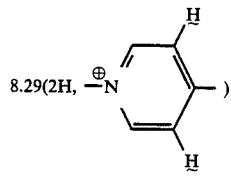)

9.14(2H, 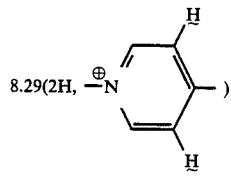)

EXAMPLE 15

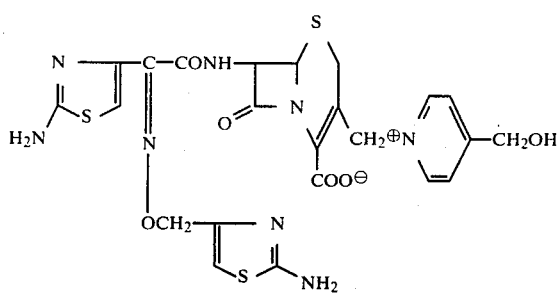

In 7 ml of water were dissolved 7.48 g of potassium iodide, 126 mg of sodium hydrogencarbonate, 1.635 g of 4-pyridinemethanol, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid, and the mixture was stirred for 10 hours at 56°–75° C.

The reaction mixture was cooled and then applied to column chromatography on Diaion HP-20. The product was eluted first with water and then with mixtures of water and methanol while successively changing the mixing ratio and the fractions containing the desired product were collected, concentrated, and lyophilized to provide 90 mg of (Z)-7-{α-(2-amino-4-thiazolyl)-α-[(2-amino-4-thiazolyl)methoxyimino]acetamido}-3-(4-hydroxymethyl-1-pyridiniomethyl)-3-cephem-4-carboxylate.

NMR (DMSO-d₆): δ(ppm):

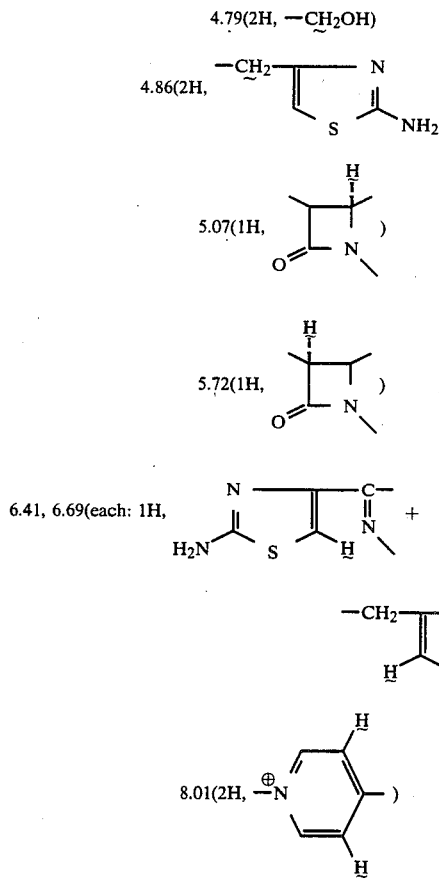

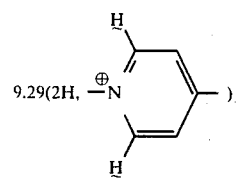

EXAMPLE 16

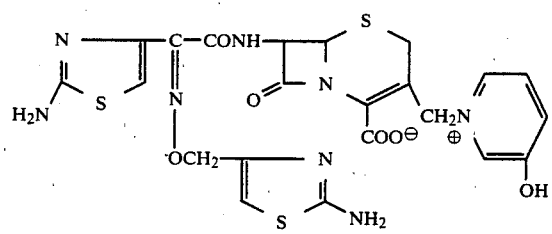

In 7 ml of water were dissolved 7.48 g of potassium iodide, 126 mg of sodium hydrogencarbonate, 1.425 g of 3-hydroxypyridine, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 12 hours at 56°–58° C.

The reaction mixture was cooled and applied to column chromatography of Diaion HP-20. The product was eluted first with water and then with mixtures of water and methanol while successively changing the mixing ratio and the fractions containing the desired product were collected, concentrated, and lyophilized to provide 63 mg of (Z)-7-{α-(2-amino-4-thiazolyl)-α-[(2-amino-4-thiazolyl)methoxyimino]acetamido}-3-(3-hydroxy-1-pyridiniomethyl)-3-cephem-4-carboxylate.

NMR (DMSO-d₆): δ(ppm):

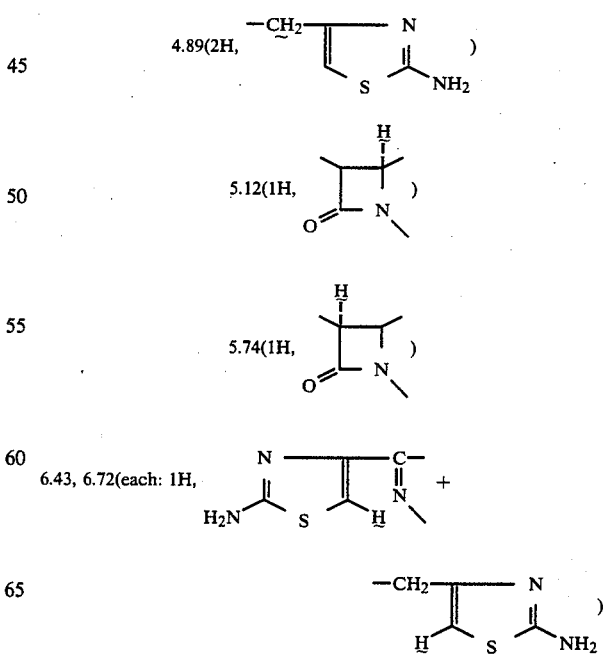

7.89(2H, 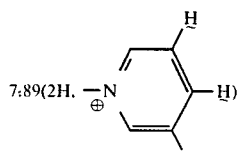)

8.61(1H, 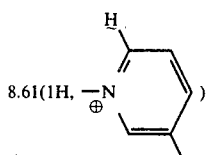)

8.87(1H, 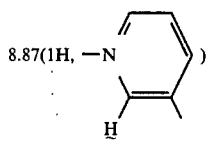)

EXAMPLE 17

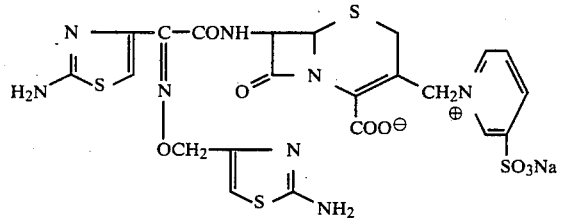

In 7 ml of water were dissolved 7.48 g of potassium iodide, 1.26 g of sodium hydrogencarbonate, 2.38 g of 3-pyridinesulfonic acid, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–58° C.

The reaction mixture was cooled and applied to column chromatography of Diaion HP-20. The product was eluted first with water and then with mixtures of water and methanol while successively changing the mixing ratio and the fractions containing the desired product were collected, concentrated, and lyophilized to provide 120 mg of (Z)-7-{α-(2-amino-4-thiazolyl)-α-[(2-amino-4-thiazolyl)methoxyimino]acetamido}-3-(3-sulfonate-1-pyridiniomethyl)-3-cephem-4-carboxylate mono-sodium salt.

NMR (DMSO-d$_6$): δ(ppm):

4.87 (2H, 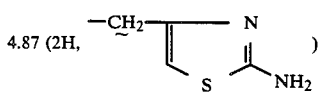)

5.08 (1H, 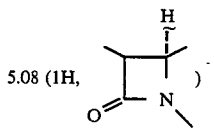)

5.68 (1H, 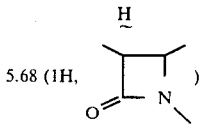)

6.44, 6.70 (each: 1H, 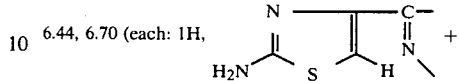)

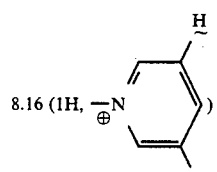

8.16 (1H, 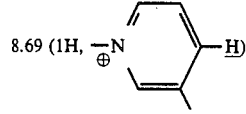)

8.69 (1H, 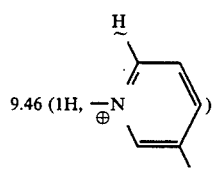)

9.46 (1H, 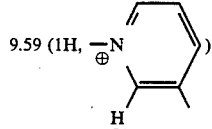)

9.59 (1H, 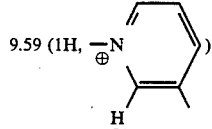)

EXAMPLE 18

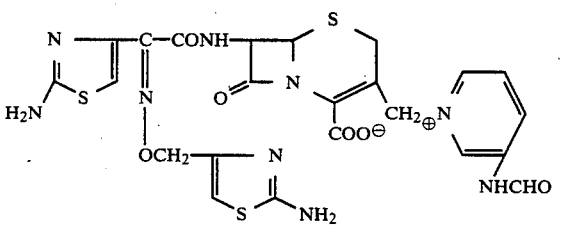

In 7 ml of water were dissolved 7.48 g of sodium iodide, 252 mg of sodium hydrogencarbonate, 1.83 g of 3-formamidopyridine, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56° to 58° C.

The reaction mixture was cooled and applied to column chromatography of Diaion HP-20. The product was eluted first with water and then with mixtures of water and methanol while successively changing the mixing ratio and the fractions containing the desired product was collected, concentrated, and lyophilized to provide 122 mg of (Z)-7-{α-(2-amino-4-thiazolyl)-α-[(2-amino-4-thiazolyl)methoxyimino]acetamido}-3-(3-formamido-1-pyridiniomethyl)-3-cephem-4-carboxylate.

NMR (DMSO-d$_6$): δ(ppm):

4.88 (2H, 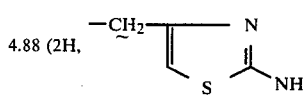)

5.09 (1H, 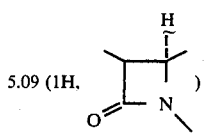)

5.73 (1H, 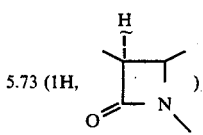)

6.43, 6.71 (each: 1H, 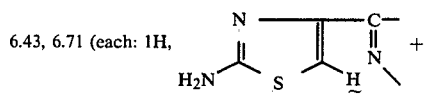 +

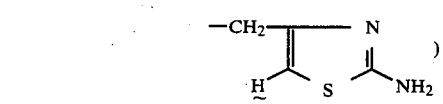)

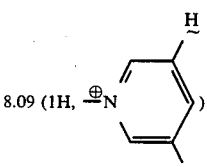

8.09 (1H, )

8.51 (1H, —NHCHO)

8.70 (1H, 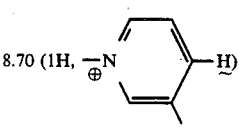)

9.16 (1H, 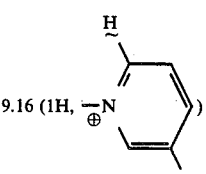)

9.63 (1H, 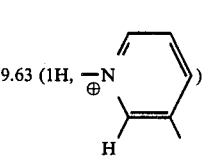)

EXAMPLE 19

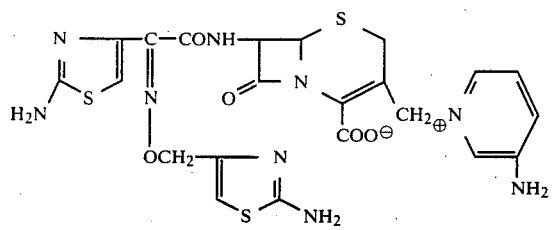

In 6 ml of methanol was suspended 396 mg of (Z)-7-{α-(2-amino-4-thiazolyl)-α-[(2-amino-4-thiazolyl)methoxyimino]acetamido}-3-(3-formamido-1-pyridiniomethyl)-3-cephem-4-carboxylate and after adding 2.6 ml of concentrated hydrochloric acid under ice-cooling, the mixture was stirred for 80 minutes at 20°–23° C.

The reaction mixture was concentrated up to about 3 ml and the concentrate was poured into 300 ml of water. Then, after adjusting the pH of the solution to about 7 with an aqueous sodium hydrogencarbonate solution, the solution was applied to column chromatography of Diaion HP-20. The product was eluted first with water and then with mixtures of water and methanol while successively changing the mixing ratio and the fractions containing the product were collected, concentrated, and lyophilized to provide 78 mg of (Z)-7-{α-(2-amino-4-thiazolyl)-α-[(2-amino-4-thiazolyl)methoxyimino]acetamido}-3-(3-amino-1-pyridiniomethyl)-3-cephem-4-carboxylate.

NMR (DMSO-d$_6$): δ(ppm):

4.91 (2H, 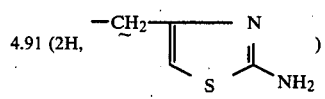)

5.07 (1H, 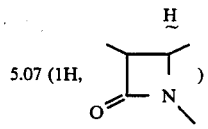)

5.69 (1H, 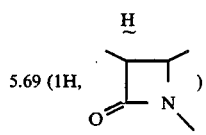)

6.44, 6.72 (each: 1H, 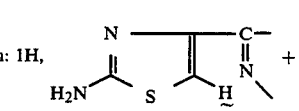 +

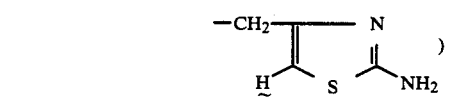)

7.65 (1H, 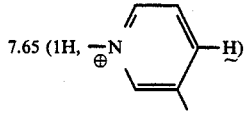)

7.70 (1H, 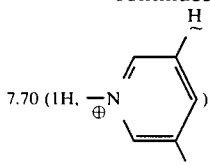)

8.39 (1H, 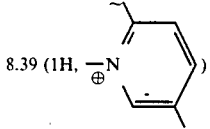)

8.52 (1H, 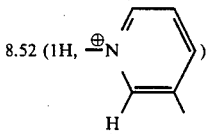)

EXAMPLE 20

5.09 (1H, 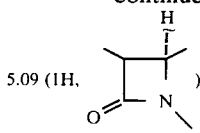)

5.71 (1H, 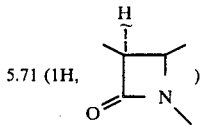)

6.41, 6.70 (each: 1H, 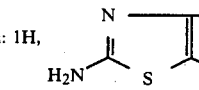

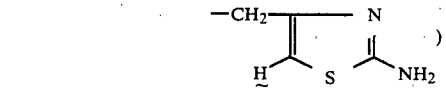)

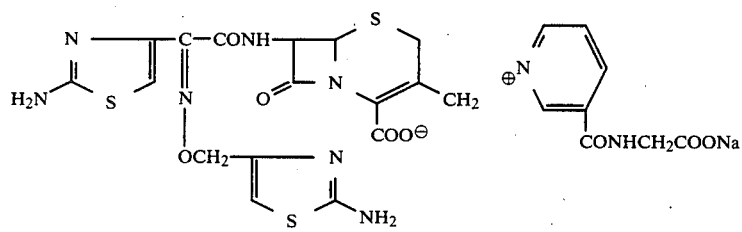

In 7 ml of water were dissolved 7.48 g of sodium iodide, 1.26 g of sodium hydrogencarbonate, 2.7 g of nicotinylglycine, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 58°–59° C.

The reaction mixture was cooled and applied to column chromatography of Diaion HP-20. The product was eluted first with water and then mixtures of water and methanol while successively changing the mixing ratio and the fractions containing the desired product were collected, concentrated, and lyophilized to provide 63 mg of (Z)-7-{α-(2-amino-4-thiazolyl)-α-[(2-amino-4-thiazolyl)methoxyimino]acetamido}-3-{3-[N-(carboxylatemethyl)carbamoyl]-1-pyridiniomethyl}-3-cephem-4-carboxylate mono-sodium salt.

NMR (DMSO-$d_6$): δ(ppm):

3.96 (2H, —CONH.CH$_2$COO$^-$)

4.87 (2H, 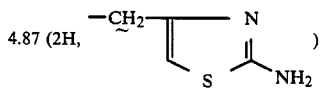)

8.29 (1H, 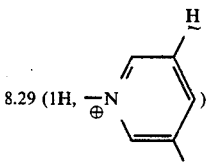)

8.97 (1H, 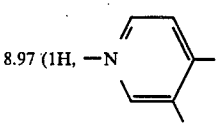)

9.70 (1H, 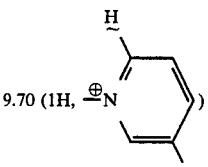)

9.76 (1H, 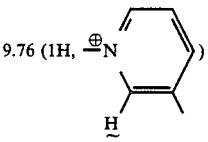)

EXAMPLE 21

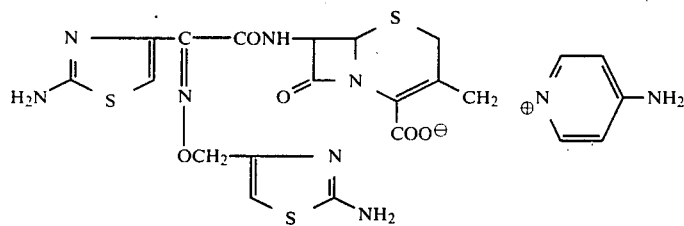

In 7 ml of water were dissolved 7.48 g of sodium iodide, 252 mg of sodium hydrogencarbonate, 1.83 g of 4-formamidopyridine, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 9 hours at 59°-60° C.

The reaction mixture was cooled and applied to column chromatography of Diaion HP-20 and the product was eluted with a mixture of water and methanol (7.5:2.5). The fraction was lyophilized to provide 115 mg of a crude product. The crude product was suspended in 1.5 mg of methanol and after adding thereto 0.62 ml of concentrated hydrochloric acid under ice-cooling, the mixture was stirred for one hour at 20°-23° C. The reaction mixture was concentrated in order to remove methanol, the concentrate was added to 60 ml of water, and after adjusting the pH of the solution to 7 with an aqueous sodium hydrogencarbonate, and the solution was applied to column chromatography of Diaion HP-20. The product was eluted with a mixture of water and methanol (7.5:2.5) and the fraction was lyophilized to provide 18 mg of 7-{α-(2-amino-4-thiazolyl)-α-[(2-amino-4-thiazolyl)methoxyimino]acetamido}-3-(4-amino-1-pyridiniomethyl)-3-cephem-4-carboxylate.

NMR (DMSO-d₆): δ(ppm):

-continued 6.44, 6.74 (each: 1H, 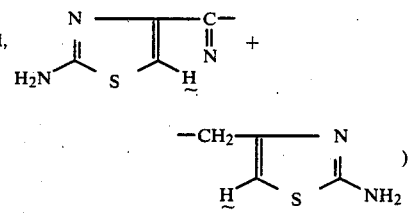 +

-CH₂  N
       )
  H  S  NH₂

6.84 (2H —N⊕— NH₂) 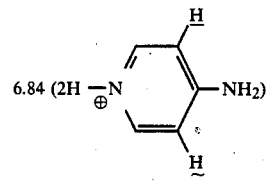

8.56 (2H —N⊕— NH₂) 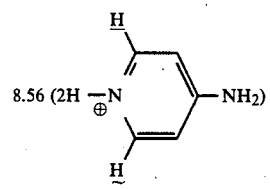

EXAMPLE 22

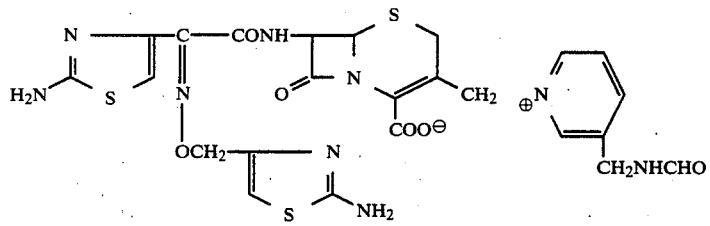

In 7 ml of water were dissolved 7.48 g of potassium iodide, 252 mg of sodium hydrogencarbonate, 2.04 g of 3-formamidomethylpyridine, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°-58° C.

The reaction mixture was cooled and applied to column chromatography of Diaion HP-20. The product was eluted first with water and then with mixtures of water and methanol while successively changing the mixing ratio and the fractions containing the desired product were collected, concentrated, and then lyophilized to provide 141 mg of (Z)-7-{α-(2-amino-4-thiazolyl)-α-[(2-amino-4-thiazolyl)methoxyimino]acetamido}-3-(3-formamidomethyl-1-pyridiniomethyl)-3-cephem-4-carboxylate.

NMR (DMSO-d₆): δ(ppm):

4.90 (2H 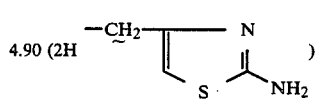 )

5.07 (1H 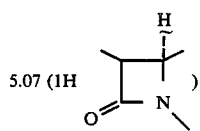 )

5.72 (1H 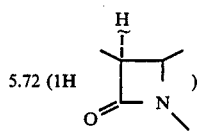 )

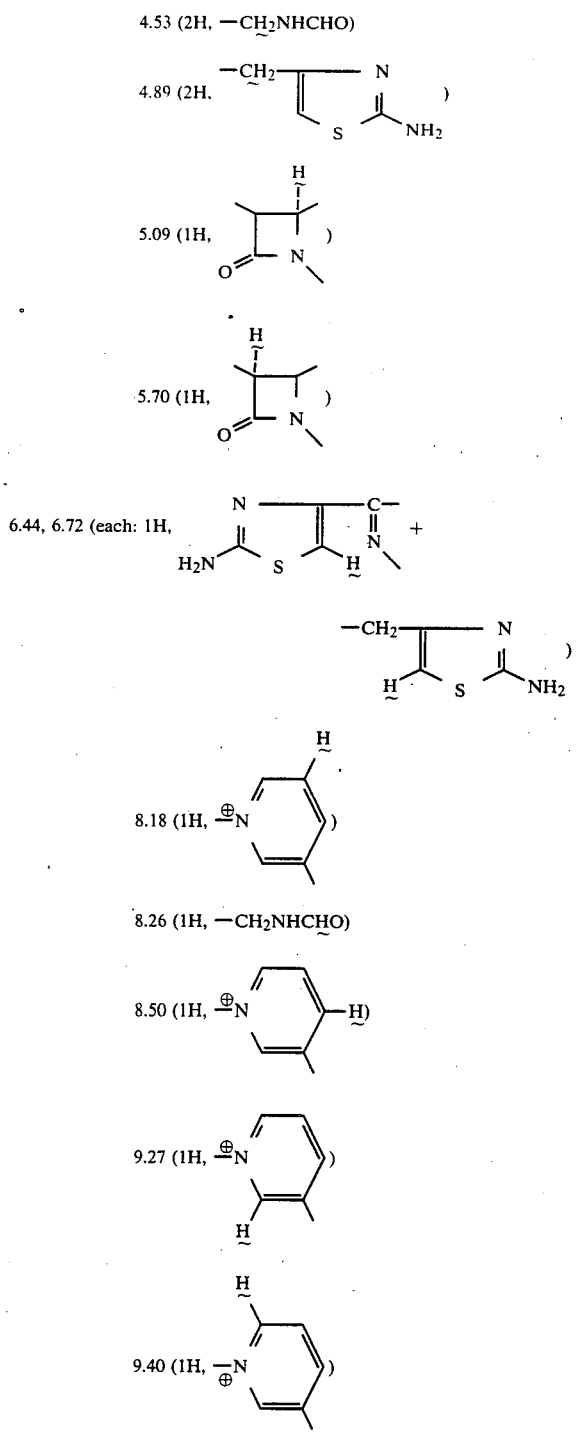

In 4 ml of dichloromethane was suspended 725 mg of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and after adding thereto 875 ml of bis(trimethylsilyl)trifluoroacetamide, the mixture was stirred for one hour at room temperature. To the solution was added 285 ml of trimethylsilyl iodide and after stirring the mixture for 40 minutes, the mixture was concentrated. The residue was dissolved in 3 ml of acetonitrile and after adding thereto 0.1 ml of tetrahydrofuran, the mixture was stirred for 5 minutes. The solution was added to another solution which was obtained by suspending 165 mg mg of 4-hydroxycarbamoylpyridine in 2 ml of acetonitrile and then adding 318 ml of bis(trimethylsilyl)trifluoroacetoamide to the formed suspension in order to dissolve the suspension. The mixture was stirred for 5 hours at room temperature.

The reaction mixture was mixed with 0.1 ml of water and a crude product thus precipitated was collected by filtration, washed with 30 ml of ether, and dried. The crude product was suspended in water and after adjusting the pH of the suspension to 8-9 with an aqueous solution of sodium hydrogencarbonate, the mixture was applied to column chromatography of Diaion HP-20. The product was eluted first with water and then with mixtures of water and methanol while successively changing the mixing ratio and the fractions containing the desired product were collected, concentrated, and lyophilized to provide 24 mg of (Z)-7-{α-(2-amino-4-thiazolyl)-α-[(2-amino-4-thiazolyl)methoxyimino]acetamido}-3-(4-hydroxycarbamoyl-1-pyridiniomethyl)-3-cephem-4-carboxylate.

NMR (DMSO-d$_6$): δ(ppm):

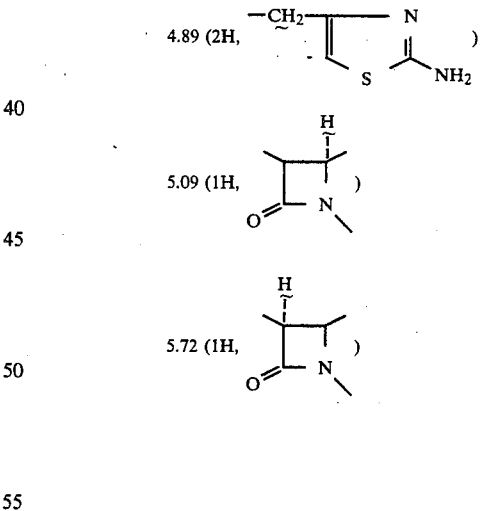

EXAMPLE 23

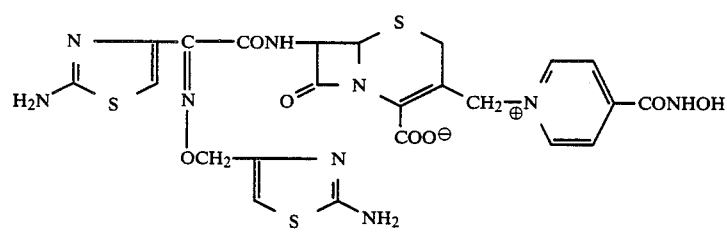

6.42, 6.72 (each: 1H, 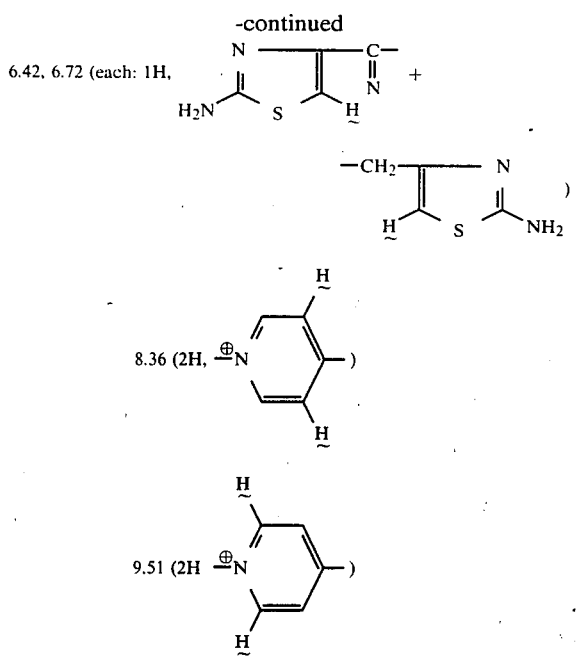

8.36 (2H, 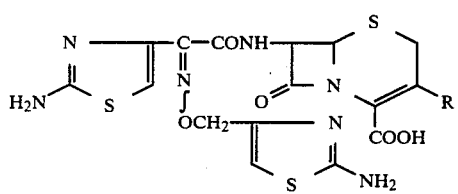)

9.51 (2H, 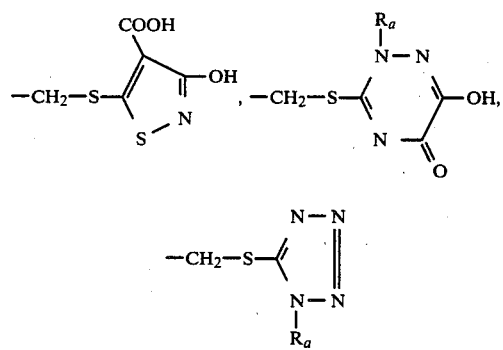)

What is claimed is:
1. A cephem compound represented by the formula

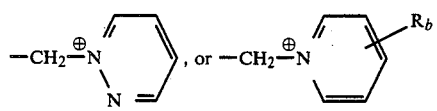

wherein R represents a lower alkyl group, which may be substituted by a lower acyloxy group, a lower alkylthio group,

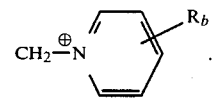

(wherein $R_a$ represents a hydrogen atom or a lower alkyl group),

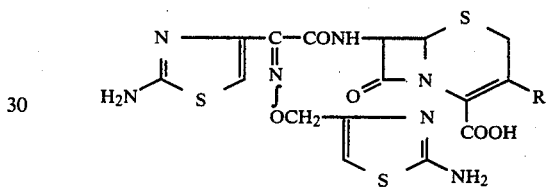

[wherein $R_b$ represents a hydrogen atom, $(CH_2)_mCOOH$, $(CH_2)_mOH$, $(CH_2)_mNH_2$, $(CH_2)_mSO_3H$, or $CONH-R'$ ($R'$ represents a hydrogen atom, a hydroxy group, or $(CH_2)_nCOOH$, m represents 0 or an integer of 1 to 3; and n represents an integer of 1 to 3)] and salts thereof.

2. The compound as claimed in claim 1 wherein said compound is a syn isomer.

3. The compound as claimed in claim 2 wherein R is a group shown by

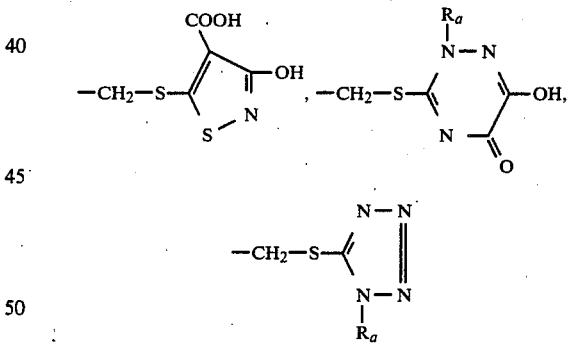

4. The compound as claimed in claim 3 wherein $R_b$ is an amino group.

5. The compound as claimed in claim 4 wherein said compund is 7-{α-(2-amino-4-thiazolyl)-α-[(2-amino-4-thiazolyl)methoxyimino]acetamido}-3-(3-amino-1-pyridiniomethyl)-3-cephem-4-carboxylate (syn isomer).

6. The compound as claimed in claim 4 wherein said compound is 7-{α-(2-amino-4-thiazolyl)-α-[(2-amino-4-thiazolyl)methoxyimino]acetamido}-3-(4-amino-1-pyridiniomethyl)-3-cephem-4-carboxylate (syn isomer).

7. A prophylaxis and treatment agent for bacterial infectious diseases comprising, as the effective component, a cephem compound represented by the formula

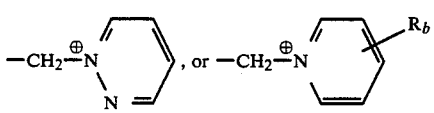

wherein R represents a lower alkyl group, which may be substituted by lower acyloxy group, a lower alkylthio group,

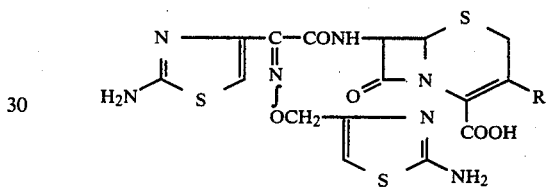

(wherein $R_a$ represents a hydrogen atom or a lower alkyl group),

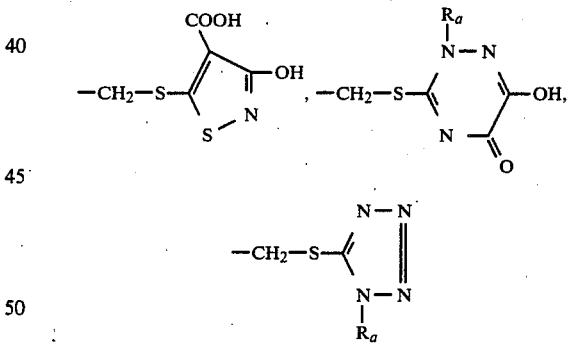

[wherein $R_b$ represents a hydrogen atom, $(CH_2)_mCOOH$, $(CH_2)_mOH$, $(CH_2)_mNH_2$, $(CH_2)_mSO_3H$, or $CONH-R'$ (wherein $R'$ represents a hydrogen atom, a hydroxy group, or $(CH_2)_nCOOH$, m represents 0 or an integer of 1 to 3; and n represents an integer of 1 to 3)] or a pharmaceutically acceptable salt thereof.

* * * * *